United States Patent
Darteil et al.

(10) Patent No.: US 12,030,861 B1
(45) Date of Patent: Jul. 9, 2024

(54) L-LYSINE SALT OF 4-CHLORO-5-[4-(2,6-DICHLOROPHENYL)SULFONYLPIPERAZIN-1-YL]-1-BENZOFURAN-2-CARBOXYLIC ACID AND VARIOUS FORMS THEREOF

(71) Applicant: ENYO PHARMA, Lyons (FR)

(72) Inventors: Raphaël Darteil, Lyons (FR); Jacky Vonderscher, Senouillac (FR); Diane Sampson, Valbonne (FR); Nicolas Philippon, L'Haÿ-les-Roses (FR); Joël Vacus, Saint Maurice-Montcouronne (FR); Julien Leroudier, Buchelay (FR); Sandra Werner, Ostwald (FR); Françoise Richard-Tiberghien, Geispolsheim (FR)

(73) Assignee: ENYO PHARMA, Lyons (FR)

( * ) Notice: Subject to any disclaimer, the term of this patent is extended or adjusted under 35 U.S.C. 154(b) by 0 days.

(21) Appl. No.: 18/351,587

(22) Filed: Jul. 13, 2023

(51) Int. Cl.
*C07D 307/85* (2006.01)
*A61K 45/06* (2006.01)

(52) U.S. Cl.
CPC ............ *C07D 307/85* (2013.01); *A61K 45/06* (2013.01); *C07B 2200/13* (2013.01)

(58) Field of Classification Search
CPC .... C07D 307/85; A61K 45/06; C07B 2200/13
See application file for complete search history.

(56) References Cited

U.S. PATENT DOCUMENTS

2022/0249469 A1* 8/2022 Vonderscher ............. A61P 3/00
2022/0265619 A1* 8/2022 Brees ................. A61K 31/7056

OTHER PUBLICATIONS

Abou-Taleb et al., Exploration of the Safety and Solubilization, Dissolution, Analgesic Effects of Common Basic Excipients on the NSAID Drug Ketoprofen, Pharmaceutics, vol. 15, 1-15, Feb. 20, 2023 (Year: 2023).*
Variankaval et al., From Form to Function: Crystallization of Active Pharmaceutical Ingredients, AIChE Journal, vol. 54, No. 7, Jul. 2008 (Year: 2008).*

* cited by examiner

*Primary Examiner* — Kortney L. Klinkel
*Assistant Examiner* — Padmaja S Rao
(74) *Attorney, Agent, or Firm* — SALIWANCHIK, LLOYD & EISENSCHENK

(57) ABSTRACT

An L-lysine salt of 4-chloro-5-[4-(2,6-dichlorophenyl)sulfonylpiperazin-1-yl]-1-benzofuran-2-carboxylic acid and forms thereof are provided. Also provided are pharmaceutical or veterinary compositions comprising this L-lysine salt and their use for treating a number of diseases.

48 Claims, 4 Drawing Sheets

L-LYSINE SALT OF 4-CHLORO-5-[4-(2,6-DICHLOROPHENYL) SULFONYLPIPERAZIN-1-YL]-1-BENZOFURAN-2-CARBOXYLIC ACID AND VARIOUS FORMS THEREOF

FIELD OF THE INVENTION

The present invention relates to the medicinal field and, more specifically, it relates to a new salt of 4-chloro-5-[4-(2,6-dichlorophenyl)sulfonylpiperazin-1-yl]-1-benzofuran-2-carboxylic acid, its different forms, methods for preparing the same, and uses for treating a number of diseases.

BACKGROUND OF THE INVENTION 4-chloro-5-[4-(2,6-dichlorophenyl)sulfonylpiperazin-1-yl]-1-benzofuran-2-carboxylic acid (IUPAC name), CAS No. 1192171-69-9, also currently known as "Vonafexor" or "PLX007", is also referenced herein as "EYP001" or "EYP-001". EYP001 has been proven to be an efficient FXR agonist and, in particular, for treating diseases or disorders related to the activity of the FXR receptors including hyperlipoproteinemia, hypertriglyceridemia, dyslipidemia, lipodystrophy, cholestasis/fibrosis, cholesterol gallstone disease, gastrointestinal disease or condition, hyperglycemia, diabetes mellitus, type 2 diabetes, insulin resistance, metabolic inflexibility, nephropathy, liver diseases, atherosclerosis, cancer, inflammatory disorders, obesity, osteoporosis, skin aging, hair growth regulation and pigmentation disorders, Parkinson's disease and/or Alzheimer's disease.

While the therapeutic effects of EYP001 free acid have been widely studied, they are limited due to its pharmaceutical properties. To date, EYP001 has been only studied in its free acid forms.

SUMMARY OF THE INVENTION

Provided herein is a new salt of EYP001, which has improved properties. More specifically, provided herein is an L-lysine salt of 4-chloro-5-[4-(2,6-dichlorophenyl)sulfonylpiperazin-1-yl]-1-benzofuran-2-carboxylic acid (EYP001). It has better solubility then, for instance, the free acid form of EYP001 and other salts, particularly in the gastrointestinal tract. It also has improved pharmacokinetics properties. As a result, a higher bioavailability can be achieved relative to the free acid form of EYP001.

Different forms of the L-lysine salt of EYP001 have been observed and/or isolated, including a number of crystalline forms. Particularly, crystalline form I, which presents excellent thermal stability (melting point: 264° C.) and is non-hygroscopic, has been isolated.

Thus, provided herein is an L-lysine salt of 4-chloro-5-[4-(2,6-dichlorophenyl)sulfonylpiperazin-1-yl]-1-benzofuran-2-carboxylic acid (EYP001) in a crystalline form (form I), wherein the X-ray diffraction pattern of the crystalline form comprises peaks at the following diffraction angles 2-Theta (2θ): 7.6°±0.2°, 10.1°±0.2°, 12.6°±0.2°, 15.1°±0.2°, 17.6°±0.2°, and 20.1°±0.2°, wherein the X-ray diffraction pattern is obtained with a Cu Kα anode. In a preferred embodiment, this crystalline form of the L-lysine salt of EYP001 is such that the X-ray diffraction pattern thereof comprises peaks at the following diffraction angles 2-Theta (2θ): 5.2°±0.2°, 7.6°±0.2°, 10.1°±0.2°, 11.6°±0.2°, 12.6°±0.2°, 13.7°±0.2°, 15.1°±0.2°, 16.3°±0.2°, 17.1°±0.2°, 17.6°±0.2°, 19.2°±0.2°, 20.1°±0.2°, 20.9°±0.2°, 22.1°±0.2°, 23.3°±0.2°, 24.0°±0.2°, 24.5°±0.2°, 25.9°±0.2°, 27.8°±0.2°, 28.7°±0.2°, 29.3°±0.2°, 30.3°±0.2°, 35.5°±0.2°, and 38.1°±0.2°, wherein the X-ray diffraction pattern is obtained with a Cu Kα anode.

In a more preferred embodiment, the crystalline form of the L-lysine salt of EYP001 is such that the X-ray diffraction pattern of the crystalline form comprises the following peaks:

| Angle 2-Thêta (°) | Inter-reticular distance (Å) | Intensity c.p.s. | % |
|---|---|---|---|
| 5.2 | 17.1 | 2621 | 12.8 |
| 7.6 | 11.7 | 7592 | 37.2 |
| 8.6 | 10.2 | 472 | 2.3 |
| 9.1 | 9.7 | 563 | 2.8 |
| 10.1 | 8.8 | 13162 | 64.5 |
| 11.6 | 7.6 | 3002 | 14.7 |
| 12.6 | 7.0 | 15458 | 75.7 |
| 13.7 | 6.5 | 1636 | 8.0 |
| 14.2 | 6.3 | 1200 | 5.9 |
| 14.4 | 6.1 | 1447 | 7.1 |
| 15.1 | 5.9 | 20420 | 100.0 |
| 15.9 | 5.6 | 714 | 3.5 |
| 16.3 | 5.4 | 2179 | 10.7 |
| 16.6 | 5.3 | 454 | 2.2 |
| 17.1 | 5.2 | 2009 | 9.8 |
| 17.6 | 5.0 | 16409 | 80.4 |
| 18.4 | 4.8 | 801 | 3.9 |
| 18.8 | 4.7 | 1255 | 6.1 |
| 19.2 | 4.6 | 1586 | 7.8 |
| 20.1 | 4.4 | 9957 | 48.8 |
| 20.5 | 4.3 | 1145 | 5.6 |
| 20.9 | 4.2 | 3149 | 15.4 |
| 21.7 | 4.1 | 948 | 4.6 |
| 22.1 | 4.0 | 1717 | 8.4 |
| 23.3 | 3.8 | 3652 | 17.9 |
| 24.0 | 3.7 | 2548 | 12.5 |
| 24.5 | 3.6 | 1778 | 8.7 |
| 24.8 | 3.6 | 971 | 4.8 |
| 25.1 | 3.5 | 1029 | 5.0 |
| 25.9 | 3.4 | 2887 | 14.1 |
| 26.7 | 3.3 | 624 | 3.1 |
| 27.8 | 3.2 | 3360 | 16.5 |
| 28.4 | 3.1 | 641 | 3.1 |
| 28.7 | 3.1 | 1184 | 5.8 |
| 29.0 | 3.1 | 713 | 3.5 |
| 29.3 | 3.0 | 1928 | 9.4 |
| 30.3 | 2.9 | 4176 | 20.5 |
| 30.9 | 2.9 | 447 | 2.2 |
| 31.2 | 2.9 | 506 | 2.5 |
| 31.6 | 2.8 | 459 | 2.2 |
| 32.7 | 2.7 | 336 | 1.6 |
| 33.2 | 2.7 | 466 | 2.3 |
| 33.7 | 2.7 | 372 | 1.8 |
| 34.1 | 2.6 | 538 | 2.6 |
| 34.9 | 2.6 | 413 | 2.0 |
| 35.5 | 2.5 | 2284 | 11.2 |
| 36.3 | 2.5 | 688 | 3.4 |
| 36.6 | 2.5 | 460 | 2.3 |
| 36.9 | 2.4 | 362 | 1.8 |
| 37.4 | 2.4 | 346 | 1.7 |
| 38.1 | 2.4 | 1043 | 5.1 |
| 38.8 | 2.3 | 391 | 1.9 |
| 40.5 | 2.2 | 514 | 2.5 |
| 40.9 | 2.2 | 315 | 1.5 |
| 41.3 | 2.2 | 369 | 1.8 |
| 42.5 | 2.1 | 335 | 1.6 |
| 43.0 | 2.1 | 342 | 1.7 |
| 43.5 | 2.1 | 315 | 1.5 |
| 43.7 | 2.1 | 489 | 2.4 |
| 44.9 | 2.0 | 364 | 1.8 |
| 45.3 | 2.0 | 304 | 1.5 |
| 45.6 | 2.0 | 310 | 1.5 |

-continued

| Angle 2-Thêta (°) | Inter-reticular distance (Å) | Intensity c.p.s. | % |
|---|---|---|---|
| 46.1 | 2.0 | 337 | 1.7 |
| 47.7 | 1.9 | 327 | 1.6 |
| 48.5 | 1.9 | 251 | 1.2 |
| 48.9 | 1.9 | 266 | 1.3 |
| 49.2 | 1.9 | 276 | 1.4 | wherein the X-ray diffraction pattern is obtained with a Cu Kα anode.

Another aspect of the invention is a process for preparing an L-lysine salt of 4-chloro-5-[4-(2,6-dichlorophenyl)sulfonylpiperazin-1-yl]-1-benzofuran-2-carboxylic acid, preferably a crystalline form of an L-lysine salt of EYP001 comprising the steps of:
 a) contacting a solution of 4-chloro-5-[4-(2,6-dichlorophenyl)sulfonylpiperazin-1-yl]-1-benzofuran-2-carboxylic acid in THF to a solution of L-lysine in Ethanol/water or in water;
 b) optionally triggering the formation of a crystalline form, and/or optionally improving the crystallinity of the crystalline form; and
 c) isolating the crystalline form obtained in step b) or a).

In a particular embodiment, the step a) is carried on such that 4-chloro-5-[4-(2,6-dichlorophenyl)sulfonylpiperazin-1-yl]-1-benzofuran-2-carboxylic acid:L-lysine stoichiometry is about 1:1.

In a further particular embodiment, the improvement of the crystallinity of step b) is performed by a temperature cycling, preferably the temperature cycling is repeated several times, more preferably 2 or 3 times.

A further aspect of the invention is an L-lysine salt of EYP001 or a crystalline form of an L-lysine salt of EYP001 as defined herein for use as a drug or a medicine.

Another aspect of the invention is a pharmaceutical or veterinary composition comprising an L-lysine salt of EYP001 or a crystalline form of an L-lysine salt of EYP001 as defined herein, and a pharmaceutically acceptable excipient.

In a particular embodiment, the pharmaceutical or veterinary composition as defined herein further comprises an additional therapeutic agent, for instance a TLR3 agonist, a TLR7 agonist, a TLR8 agonist, a TLR9 agonist, a RIG-I modulator, a STING agonist, an antiviral agent, such as Bulevirtide, an antibacterial agent, an interferon or a pegylated form thereof, a checkpoint inhibitor such as a PD-1 or PD-L1 agonist, an ERA, an ACE inhibitor, an ARB, a RASS antagonist, a beta-blocker, a diuretic agent, a MRA, a SGLT2 inhibitor, a GLP1 agonist, a SGLT1 inhibitor, FGF19, FGF21, a DPP-4 inhibitor, a PPAR agonist, a THR beta agonist, a FASN, an inhibitor of HSD17b13 or a combination thereof.

Another aspect of the invention is a pharmaceutical or veterinary composition as defined herein for use for the treatment of a disease selected from the group consisting of a chronic liver disease, a gastrointestinal disease, a renal disease, a cardiovascular disease, a metabolic disease, an infection, a cancer, and an autoimmune disease.

In a particular aspect, the disease is an infection, especially a chronic infection, preferably a viral infection, more preferably an infection by hepatitis B virus (HBV), hepatitis C virus (HCV), hepatitis D virus (HDV), herpes simplex virus (HSV), papillomavirus (HPV) (e.g., condylomata acuminate), varicella-zoster virus, cytomegalovirus (CMV), rhinoviruses, hepatitis A virus, hepatitis E virus, Kaposis sarcoma herpesvirus, coronavirus including SARS-Cov1, MERS-Cov and SARS-Cov2, retrovirus including HIV, and influenza virus. Particularly, the pharmaceutical or veterinary composition for use for the treatment of an infection is to be used in combination with a TLR3 agonist, a TLR7 agonist, a TLR8 agonist, a TLR9 agonist, a RIG-I modulator, a STING agonist, an antiviral agent, such as Bulevirtide, an antibacterial agent, an interferon or a pegylated form thereof, a checkpoint inhibitor such as a PD-1 or PD-L1 agonist, or a combination thereof.

In a further particular aspect, the disease is a renal disease, especially a renal disease comprising renal fibrosis and/or Chronic Kidney Disease (CKD), for instance selected from the group consisting of hypertension, type 2 diabetes, type 1 diabetes, obesity, Non-Alcoholic Steatohepatitis (NASH), non-alcoholic fatty liver disease (NAFLD), metabolic (dysfunction) associated fatty liver disease (MAFLD), ageing, infectious glomerulonephritis, in particular infections such as syphilis, malaria, hepatitis B, hepatitis C or HIV, focal segmental glomerulosclerosis, IgA nephropathy, minimal change glomerulopathy, membranous nephropathy, renal vasculitis, urinary tract obstruction, genetic alterations, autoimmune diseases such as systemic lupus erythematosus (SLE), and drug- or toxin-induced nephropathy such as nephropathy induced by drugs such as captopril, NSAIDs, penicillamine, probenecid, bucillamine, anti-TNF therapy, and tiopronin or by toxins such as inorganic salts (e.g., gold, mercury), AIDS-associated nephropathy, ischemic nephropathy, tubulointerstitial nephropathy, hepatorenal syndrome, hydronephrosis, renal dysplasia, medullary cystic kidney disease, medullary sponge kidney, multicystic dysplastic kidney, podocytopathy, kidney papillary necrosis, nephritis including glomerulonephritis, hereditary nephritis, interstitial nephritis, pyelitis, nephrocalcinosis, nephrosclerosis, Alport syndrome cystinosis, classical homocystinuria (HCU), Fabry's disease, renal sarcoidosis, diabetic nephropathy, focal segmental glomerulosclerosis (FSGS), hypertensive nephrosclerosis, chronic glomerulonephritis, chronic transplant glomerulopathy, chronic interstitial nephritis, Sjogren's syndrome, Alagille syndrome, alpha 1-antitrypsin deficiency, and polycystic kidney disease. Particularly, the pharmaceutical or veterinary composition for use for the treatment of a renal disease is to be used in combination with an ERA, an ACE inhibitor, an ARB, a RASS antagonist, a beta-blocker, a diuretic agent, a MRA, a SGLT2 inhibitor, a GLP1 agonist or a combination thereof.

In a further particular aspect, the disease is a liver disease, especially a chronic liver disease, preferably primary biliary cirrhosis or primary biliary cholangitis (PBC), cerebrotendinous xanthomatosis (CTX), primary sclerosing cholangitis (PSC), drug induced cholestasis, intrahepatic cholestasis of pregnancy, parenteral nutrition associated cholestasis (PNAC), bacterial overgrowth or sepsis associated cholestasis, autoimmune hepatitis, chronic viral hepatitis, alcoholic liver disease, nonalcoholic fatty liver disease (NAFLD), nonalcoholic steatohepatitis (NASH), metabolic-associated fatty liver disease (MAFLD), alcoholic hepatitis, liver transplant associated graft versus host disease, living donor transplant liver regeneration, congenital hepatic fibrosis, choledocholithiasis, granulomatous liver disease, intra- or extrahepatic malignancy, Sjogren's syndrome, Alagille syndrome, Sarcoidosis, Wilson's disease, Gaucher's disease, hemochromatosis, biliary atresia, ductopenic liver transplant rejection, cystic fibrosis liver disease and alpha 1-antitrypsin deficiency. Particularly, the pharmaceutical or veterinary composition for use for the treatment of a liver disease is to be used in combination with a SGLT2 inhibitor, a GLP1 agonist, a SGLT1 inhibitor, FGF19, FGF21, a DPP-4 inhibitor, a PPAR agonist, a THR beta agonist, a FASN, an inhibitor of HSD17b13 or a combination thereof.

BRIEF DESCRIPTION OF THE DRAWINGS

FIG. 3B: sample B).

DETAILED DESCRIPTION OF THE INVENTION

Definitions

Figure 1:
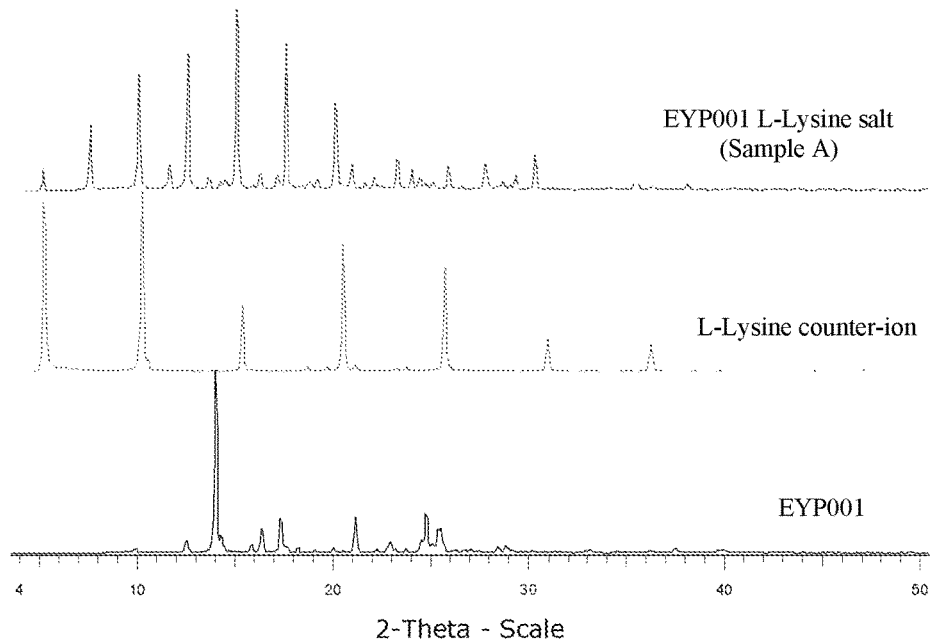
FIG. 1: Overlaid XRPD profiles of EYP001 L-lysine salt (sample A), L-lysine counter-ion, and EYP001 acid form.

Throughout this specification and in the claims that follow, the following terms have the following meanings, unless explicitly stated otherwise.

As used herein, the term "about" or "around" will be understood by one ordinary skill in the art and will vary to some extent on the context in which it is used. For instance, in a particular context, "about" or "around" may mean up to plus or minus 10% of a particular term.

As used herein, the terms "compound" or "molecule" refer to an L-lysine salt of EYP001 according to the invention including its forms as disclosed herein.

As used herein, the terms "treatment", "treat" or "treating" refer to any act intended to ameliorate the health status of patients such as therapy, prevention, prophylaxis and retardation of a disease. In certain embodiments, such terms refer to the amelioration or eradication of the disease, or symptoms associated with it. In other embodiments, this term refers to minimizing the spread or worsening of the disease, resulting from the administration of one or more therapeutic agents to a subject with such a disease.

As used herein, the terms "subject", "individual" or "patient" are interchangeable and refer to an animal, preferably to a mammal, even more preferably to a human, including adult and child. However, the term "subject" can also refer to non-human animals, in particular mammals such as dogs, cats, horses, cows, pigs, sheep and non-human primates, among others.

The terms "quantity," "amount," and "dose" are used interchangeably herein and may refer to an absolute quantification of a molecule.

As used herein, the term "therapeutic effect" refers to an effect induced by an active ingredient, or a pharmaceutical composition according to the invention, capable to prevent or to delay the appearance or development of a disease or disorder, or to cure or to attenuate the effects of a disease or disorder.

As used herein, the term "effective amount" refers to a quantity of an active ingredient or of a pharmaceutical composition which prevents, removes or reduces the deleterious effects of the disease. The quantity to be administered can be adapted by a person skilled in the art according to the subject to be treated, to the nature of the disease, etc. In particular, doses and regimen of administration may be function of the nature, of the stage and of the severity of the disease to be treated, as well as of the weight, the age and the global health of the subject to be treated, as well as of the judgment of the doctor.

As used herein, the expressions "pharmaceutically acceptable carrier" or "pharmaceutically acceptable excipient" refers to any ingredient except active ingredients that is present in a pharmaceutical composition. Its addition may be aimed to confer a particular consistency or other physical or gustative properties to the final product. A pharmaceutically acceptable carrier or a pharmaceutically acceptable excipient must be devoid of any interaction, in particular chemical, with the active ingredients.

As used herein, the terms "kit", "product" or "combined preparation" refers especially to a "kit of parts" in the sense that the combination partners as defined herein can be dosed independently or by use of different fixed combinations with distinguished amounts of the combination partners, i.e. simultaneously or at different time points. The parts of the kit of parts can then, e.g., be administered simultaneously or chronologically staggered, that is at different time points and with equal or different time intervals for any part of the kit of parts. The ratio of the total amounts of the combination partners to be administered in the combined preparation can be varied. The combination partners can be administered by the same route or by different routes.

4-chloro-5-[4-(2,6-dichlorophenyl)sulfonylpiperazin-1-yl]-1-benzofuran-2-carboxylic acid (IUPAC name; CAS No. 1192171-69-9) is also called herein 4-chloro-5-[4-(2,6-dichlorobenzene-1-sulfonyl)-piperazin-1-yl]-1-benzofuran-2-carboxylic acid or 4-chloro-5-[4-(2,6-dichloro-benzenesulfonyl)-piperazin-1-yl]-benzofuran-2-carboxylic acid, "Vonafexor", "PLX007", "EYP001", or "EYP-001", and has the following formula:

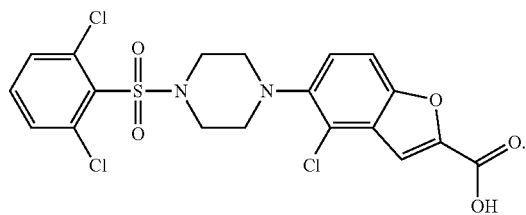 [SMILES: O=C(O)c1cc2c(Cl)c(N3CCN(S(=O)(=O)c4c(Cl)cccc4Cl)CC3)ccc2o1]

The synthesis of EYP001 free acid was first described by Merck Patent GMBH in Example 136 of WO 2009/127321. It is well understood that EYP001 can be also prepared by other synthesis routes and well-known techniques by one of ordinary skill in the art. EYP001 can even be directly purchased from commercial suppliers.

EYP001 free acid has poor solubility, which represents a major obstacle for the development of this drug. However, it has now been found that an L-lysine salt of EYP001 as provided herein has a number of improved properties compared to the free acid form and even other salts, including better solubility, and leads to better bioavailability than the free acid form. Moreover, it is suitable for pharmaceutical dosage forms.

The L-lysine salt of EYP001 can be prepared according to any methods known by one of ordinary skill in the art for preparing salts of active ingredients. For instance, EYP001 can be solubilized in a solvent, preferably a polar solvent, and the counter-ion L-lysine is added. As examples of solvents, it can be cited, without limitation, water, isopropyl acetate, ethyl acetate, dimethylsulfoxide, heptane, acetonitrile, isopropyl alcohol, ethanol, methanol, acetone, tetrahydrofuran, and mixtures thereof. Particularly, the solvent is chosen among tetrahydrofuran, water, and ethanol. Preferably, the solvent is a mixture of tetrahydrofuran, water, and ethanol.

In a particular embodiment, the L-lysine salt of EYP001 is prepared by contacting a solution of EYP001 in THF to a solution of L-lysine in water. In a further particular embodiment of the invention the L-lysine salt of EYP001 is prepared by contacting a solution of EYP001 in THF to a solution of L-lysine in ethanol/water.

A particular embodiment of the invention is therefore a process for preparing an L-lysine salt of 4-chloro-5-[4-(2, 6-dichlorophenyl)sulfonylpiperazin-1-yl]-1-benzofuran-2-carboxylic acid comprising the steps of:

a) contacting a solution of 4-chloro-5-[4-(2,6-dichlorophenyl)sulfonylpiperazin-1-yl]-1-benzofuran-2-carboxylic acid in THF to a solution of L-lysine in ethanol/water or in water; and $a_1$) isolating the L-lysine salt of 4-chloro-5-[4-(2,6-dichlorophenyl)sulfonylpiperazin-1-yl]-1-benzofuran-2-carboxylic acid obtained in step a).

Preferably, 4-chloro-5-[4-(2,6-dichlorophenyl)sulfonylpiperazin-1-yl]-1-benzofuran-2-carboxylic acid and L-lysine are used in a stoichiometry about 1:1.

Various forms of the L-lysine salt of EYP001 have been identified. Among them are various crystalline and amorphous forms.

The present invention provides crystalline forms of an L-lysine salt of EYP001 (forms I-V). These crystalline forms present further advantageous physico-chemical properties for pharmaceutical dosage forms. In particular, crystalline form I has excellent thermal stability (up to 260° C.) and is non-hygroscopic.

The crystalline forms described herein may be identified and/or characterized by various analytical techniques known to one of ordinary skill in the art. Such techniques include, but are not limited to, X-ray Powder Diffraction (XRPD), Differential Scanning Calorimetry (DSC), Thermogravimetric Analysis (TGA), Dynamic Vapor Sorption (DVS), and/or IR spectrum.

Figure 3A:
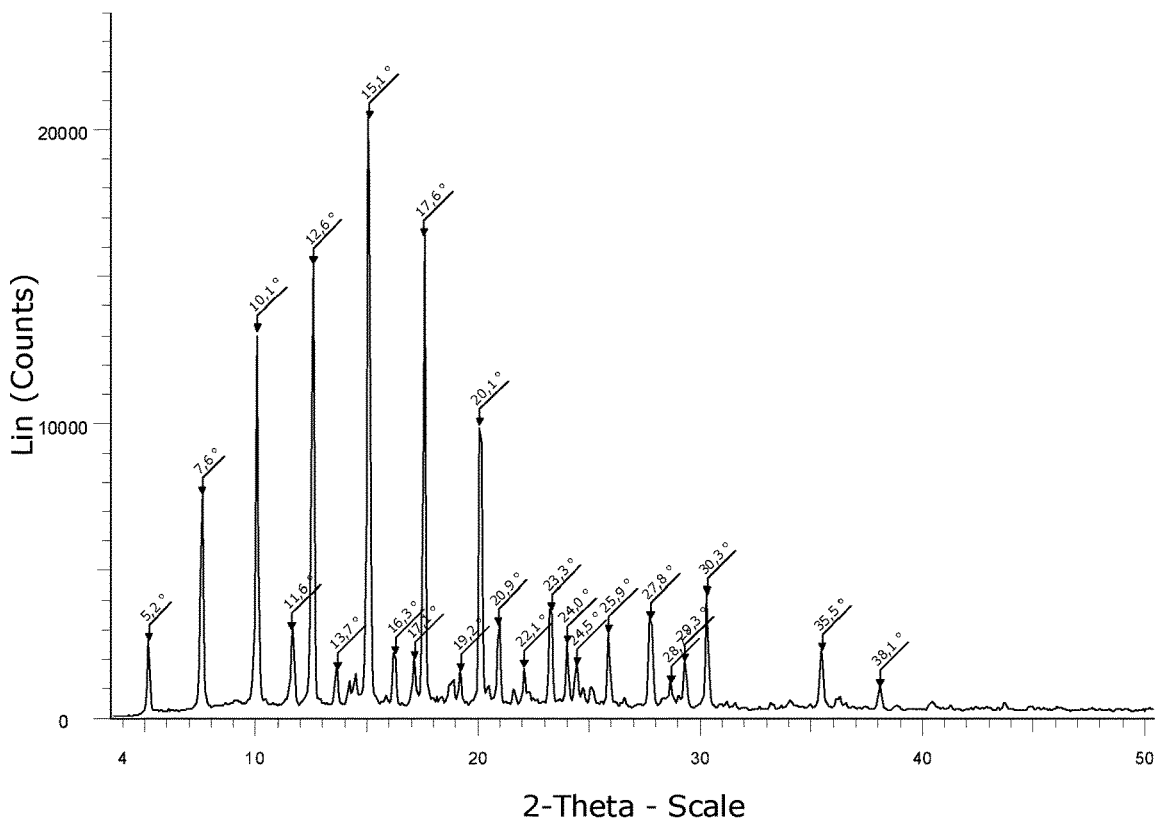
FIGS. 3A-3B: XRPD pattern of EYP001 L-lysine salt (FIG. 3A: sample A.

The crystalline form(s) of an L-lysine salt of EYP001 may be characterised in particular by X-ray diffraction pattern. Particularly, the X-ray diffraction pattern of one crystalline form (form I) comprises peaks at the following diffraction angles 2-Theta (2θ): 7.6°±0.2°, 10.1°±0.2°, 12.6°±0.2°, 15.1°±0.2°, 17.6°±0.2°, and 20.1°±0.2°, wherein the X-ray diffraction pattern is obtained with a Cu Kα anode. More particularly, the X-ray diffraction pattern of this crystalline form comprises peaks at the following diffraction angles 2-Theta (2θ): 5.2°±0.2°, 7.6°±0.2°, 10.1°±0.2°, 11.6°±0.2°, 12.6°±0.2°, 13.7°±0.2, 15.1°±0.2°, 16.3°±0.2°, 17.1°±0.2°, 17.6°±0.2°, 19.2°±0.2°, 20.1°±0.2°, 20.9°±0.2°, 22.1°±0.2°, 23.3°±0.2°, 24.0°±0.2°, 24.5°±0.2°, 25.9°±0.2°, 27.8°±0.2°, 28.7°±0.2°, 29.3°±0.2°, 30.3°±0.2°, 35.5°±0.2°, and 38.1°±0.2°, wherein the X-ray diffraction pattern is obtained with a Cu Kα anode. Still more particularly, the X-ray diffraction pattern of the crystalline form, obtained with a Cu Kα anode, comprises peaks listed in the following table 1 or by its X-ray diffraction pattern as depicted in FIG. 3A.

TABLE 1

X-Ray Peaks of Crystalline Form I of an L-lysine salt of EYP001

| Angle 2-Thêta (°) | Inter-reticular distance (Å) | Intensity c.p.s. | % |
|---|---|---|---|
| 5.2 | 17.1 | 2621 | 12.8 |
| 7.6 | 11.7 | 7592 | 37.2 |
| 8.6 | 10.2 | 472 | 2.3 |
| 9.1 | 9.7 | 563 | 2.8 |
| 10.1 | 8.8 | 13162 | 64.5 |
| 11.6 | 7.6 | 3002 | 14.7 |
| 12.6 | 7.0 | 15458 | 75.7 |
| 13.7 | 6.5 | 1636 | 8.0 |
| 14.2 | 6.3 | 1200 | 5.9 |
| 14.4 | 6.1 | 1447 | 7.1 |
| 15.1 | 5.9 | 20420 | 100.0 |
| 15.9 | 5.6 | 714 | 3.5 |
| 16.3 | 5.4 | 2179 | 10.7 |
| 16.6 | 5.3 | 454 | 2.2 |
| 17.1 | 5.2 | 2009 | 9.8 |
| 17.6 | 5.0 | 16409 | 80.4 |
| 18.4 | 4.8 | 801 | 3.9 |
| 18.8 | 4.7 | 1255 | 6.1 |
| 19.2 | 4.6 | 1586 | 7.8 |
| 20.1 | 4.4 | 9957 | 48.8 |
| 20.5 | 4.3 | 1145 | 5.6 |
| 20.9 | 4.2 | 3149 | 15.4 |
| 21.7 | 4.1 | 948 | 4.6 |
| 22.1 | 4.0 | 1717 | 8.4 |
| 23.3 | 3.8 | 3652 | 17.9 |
| 24.0 | 3.7 | 2548 | 12.5 |
| 24.5 | 3.6 | 1778 | 8.7 |
| 24.8 | 3.6 | 971 | 4.8 |
| 25.1 | 3.5 | 1029 | 5.0 |
| 25.9 | 3.4 | 2887 | 14.1 |
| 26.7 | 3.3 | 624 | 3.1 |
| 27.8 | 3.2 | 3360 | 16.5 |
| 28.4 | 3.1 | 641 | 3.1 |
| 28.7 | 3.1 | 1184 | 5.8 |
| 29.0 | 3.1 | 713 | 3.5 |
| 29.3 | 3.0 | 1928 | 9.4 |
| 30.3 | 2.9 | 4176 | 20.5 |
| 30.9 | 2.9 | 447 | 2.2 |
| 31.2 | 2.9 | 506 | 2.5 |
| 31.6 | 2.8 | 459 | 2.2 |
| 32.7 | 2.7 | 336 | 1.6 |
| 33.2 | 2.7 | 466 | 2.3 |
| 33.7 | 2.7 | 372 | 1.8 |
| 34.1 | 2.6 | 538 | 2.6 |
| 34.9 | 2.6 | 413 | 2.0 |
| 35.5 | 2.5 | 2284 | 11.2 |
| 36.3 | 2.5 | 688 | 3.4 |
| 36.6 | 2.5 | 460 | 2.3 |
| 36.9 | 2.4 | 362 | 1.8 |
| 37.4 | 2.4 | 346 | 1.7 |
| 38.1 | 2.4 | 1043 | 5.1 |
| 38.8 | 2.3 | 391 | 1.9 |
| 40.5 | 2.2 | 514 | 2.5 |
| 40.9 | 2.2 | 315 | 1.5 |
| 41.3 | 2.2 | 369 | 1.8 |
| 42.5 | 2.1 | 335 | 1.6 |
| 43.0 | 2.1 | 342 | 1.7 |
| 43.5 | 2.1 | 315 | 1.5 |
| 43.7 | 2.1 | 489 | 2.4 |
| 44.9 | 2.0 | 364 | 1.8 |
| 45.3 | 2.0 | 304 | 1.5 |
| 45.6 | 2.0 | 310 | 1.5 |
| 46.1 | 2.0 | 337 | 1.7 |
| 47.7 | 1.9 | 327 | 1.6 |
| 48.5 | 1.9 | 251 | 1.2 |
| 48.9 | 1.9 | 266 | 1.3 |
| 49.2 | 1.9 | 276 | 1.4 |

One of ordinary skill in the art will appreciate that an X-ray diffraction pattern may be obtained with a measurement error that is dependent upon the measurement conditions employed. In particular, it is generally known that intensities in an X-ray diffraction pattern may fluctuate depending upon measurement conditions employed and the shape or morphology of the particle together with the crystal size distribution. It should be further understood that relative intensities may also vary depending upon experimental conditions and, accordingly, the exact order of intensity should not be taken into account. Additionally, a measurement error of diffraction angle for a conventional X-ray diffraction pattern is typically circa±0.02° (in 2 theta) or less, preferably circa±0.01°. Consequently, it is to be understood that the crystal form of the instant invention is not limited to a crystal form that provides an X-ray diffraction pattern completely identical to the X-ray diffraction pattern depicted in FIG. 3A or described in table 1. Any crystal form that provides an X-ray diffraction pattern substantially identical to that disclosed in FIG. 3A or described in table 1 falls within the scope of the present invention. The ability to ascertain substantial identities of X-ray diffraction patterns is within the purview of one of ordinary skill in the art.

Crystalline form(s) of an L-lysine salt of EYP001 may be also characterised by Differential Scanning Calorimetry (DSC), Thermogravimetric Analysis (TGA), and Dynamic Vapor Sorption (DVS).

In a particular embodiment, a crystalline form of an L-lysine salt of EYP001 has a melting point, by Differential Scanning Calorimetry (DSC), of about 264° C. In a particular embodiment, a crystalline form of an L-lysine salt of EYP001 shows no significant weight loss, measured by thermogravimetric analysis (TGA) at the range of about 190° C. to 280° C., i.e., before and after its melting point. In a particular embodiment, a crystalline form of an L-lysine salt of EYP001 is non-hygroscopic. More specifically, the Dynamic Vapor Sorption (DVS) analysis of this crystalline form shows only 0.4% water uptake at 25° C./60% RH.

Crystalline form(s) of the invention may be prepared by a variety of methods, including for example, crystallization or recrystallization from a suitable solvent, sublimation, growth from a melt, solid state transformation from another phase, crystallization from a supercritical fluid, and spray drying. Techniques for crystallization or recrystallization of a crystalline form from a solvent mixture include, for example, evaporation of the solvent, decreasing the temperature of the solvent mixture, crystal seeding a supersaturated solvent mixture of the molecule and/or salt, freeze drying the solvent mixture, and addition of anti-solvents (counter-solvents) to the solvent mixture. Crystals of drugs, including polymorphs, methods of preparation, and characterization of drug crystals are discussed in Solid-State Chemistry of Drugs, S. R. Byrn, R. R. Pfeiffer, and J. G. Stowell, 2$^{nd}$ Edition, SSCI, West Lafayette, Ind. (1999). For crystallization techniques that employ solvent, the choice of solvent(s) is typically dependent upon one or more factors, such as solubility of the compound, crystallization technique, vapor pressure of the solvent, viscosity of the solvent and toxicity. Combinations of solvents may be employed, for example, the compound may be solubilized into a first solvent to afford a solution, followed by the addition of an anti-solvent to decrease the solubility of the compound in the solution and to afford the formation of crystals. An anti-solvent is a solvent in which the compound has a low solubility. In a particular embodiment, the solvent is chosen among water, isopropyl acetate, ethyl acetate, dimethylsulfoxide, heptane, acetonitrile, isopropyl alcohol, methanol, ethanol, acetone, tetrahydrofuran, and mixtures thereof. In a preferred embodiment, the solvent is chosen among water, tetrahydrofuran, and mixtures thereof. In a further preferred embodiment, the anti-solvent is ethanol.

An aspect of the invention is a process for preparing a crystalline form of an L-lysine salt of 4-chloro-5-[4-(2,6-dichlorophenyl)sulfonylpiperazin-1-yl]-1-benzofuran-2-carboxylic acid comprising the steps of:
  a) contacting a solution of 4-chloro-5-[4-(2,6-dichlorophenyl)sulfonylpiperazin-1-yl]-1-benzofuran-2-carboxylic acid in THF to a solution of L-lysine in ethanol/water or in water;
  b) optionally triggering the formation of a crystalline form, and/or optionally improving the crystallinity of the crystalline form; and
  c) isolating the crystalline form obtained in step b) or a).

A particular aspect of the invention is a process for preparing a crystalline form of a L-lysine salt of 4-chloro-5-[4-(2,6-dichlorophenyl)sulfonylpiperazin-1-yl]-1-benzofuran-2-carboxylic acid comprising the steps of:
  a) contacting a solution of 4-chloro-5-[4-(2,6-dichlorophenyl)sulfonylpiperazin-1-yl]-1-benzofuran-2-carboxylic acid in THF to a solution of L-lysine in water;
  b) optionally triggering the formation of a crystalline form, and/or optionally improving the crystallinity of the crystalline form, preferably by adding ethanol; and
  c) isolating the crystalline form obtained in step b) or a).

In a particular embodiment, step a) is performed in solution, in particular EYP001 is suspended in THF and L-lysine is suspended in ethanol/water, preferably in water. In a further particular embodiment, the 4-chloro-5-[4-(2,6-dichlorophenyl)sulfonylpiperazin-1-yl]-1-benzofuran-2-carboxylic acid:L-lysine stoichiometry in step a) is about 1:1.

In a particular embodiment, step b) can be performed for instance by addition of an anti-solvent, such as ethanol, when step a) is performed in solution. Step b) may also be performed by seeding the solution with a crystal of the desired crystalline form and/or applying one or several temperature cycling. In an embodiment, step b) is performed by addition of an anti-solvent, such as ethanol, when step a) is performed in solution, or by seeding the solution with a crystal of the desired crystalline form and then by applying one or several temperature cycling. This latter step is designed to improve the crystallinity and thereby the filterability and the chemical purity of the final product.

In a particular embodiment, step c) can be performed for instance by evaporation of the reaction solvent, by filtration or by centrifugation. In a further particular embodiment, step c) may further include one or several washing steps. Each step, each step part (for instance the first or second part of step b)), and/or each combination of steps (for instance the combination of step b) and step c)) of the process of the invention may be performed once, or may be repeated several times in the process of the invention, independently of the other steps or step parts.

For instance, in step b), the temperature cycling may be performed once, alternatively it can be repeated several times, preferably between 2 and 5 times, more preferably 2 or 3 times. Repetition of the succession of steps b) allows in particular increasing the crystallinity of the form.

A crystalline form obtained by the process is a further aspect of the invention.

Also provided herein are pharmaceutical or veterinary composition(s) comprising an L-lysine salt of EYP001. These compositions optionally include at least one pharmaceutically acceptable carrier or excipient. The L-lysine salt of EYP001 therein may be in crystalline form, for instance in form I.

The compound or the pharmaceutical or veterinary composition as defined herein may be administered by any conventional route of administration. In particular, the compound or the pharmaceutical or veterinary composition can be administered by a topical, enteral, oral, parenteral, intranasal, intravenous, intra-arterial, intramuscular, subcutaneous or intraocular administration and the like.

Preferably, the compound according to the invention or the pharmaceutical or veterinary composition according to the invention is administered by enteral or parenteral route of administration. When administered parenterally, the compound or the pharmaceutical or veterinary composition is preferably administered by intravenous route of administration. When administered enterally, the compound or the pharmaceutical or veterinary composition is preferably administered by oral route of administration.

The pharmaceutical composition comprising the compound of the invention is formulated in accordance with standard pharmaceutical practice (Lippincott Williams & Wilkins, 2000 and Encyclopedia of Pharmaceutical Technology, eds. J. Swarbrick and J. C. Boylan, 1988-1999, Marcel Dekker, New York) known by a person skilled in the art.

For oral administration, the composition can be formulated into conventional oral dosage forms such as tablets, capsules, powders, granules and liquid preparations such as syrups, elixirs, and concentrated drops. Nontoxic solid carriers or diluents may be used which include, for example, pharmaceutical grades of mannitol, lactose, starch, magnesium stearate, sodium saccharine, talcum, cellulose, glucose, sucrose, magnesium, carbonate, and the like. For compressed tablets, binders, which are agents which impart cohesive qualities to powdered materials, are also necessary. For example, starch, gelatin, sugars such as lactose or dextrose, and natural or synthetic gums can be used as binders. Disintegrants are also necessary in the tablets to facilitate break-up of the tablet. Disintegrants include starches, clays, celluloses, algins, gums and crosslinked polymers. Moreover, lubricants and glidants are also included in the tablets to prevent adhesion to the tablet material to surfaces in the manufacturing process and to improve the flow characteristics of the powder material during manufacture. Colloidal silicon dioxide is most commonly used as a glidant and compounds such as talc or stearic acids are most commonly used as lubricants.

For transdermal administration, the composition can be formulated into ointment, cream or gel form and appropriate penetrants or detergents could be used to facilitate permeation, such as dimethyl sulfoxide, dimethyl acetamide and dimethylformamide.

For transmucosal administration, nasal sprays, rectal or vaginal suppositories can be used. The active compound can be incorporated into any of the known suppository bases by methods known in the art. Examples of such bases include cocoa butter, polyethylene glycols (carbowaxes), polyethylene sorbitan monostearate, and mixtures of these with other compatible materials to modify the melting point or dissolution rate.

Pharmaceutical or veterinary compositions according to the invention may be formulated to release the active drug substantially immediately upon administration or at any predetermined time or time period after administration.

The compound or the pharmaceutical or veterinary composition according to the invention may be administered as a single dose or in multiple doses. Preferably, the treatment is administered regularly, preferably between every day and every month, more preferably between every day and every two weeks, more preferably between every day and every week, even more preferably the treatment is administered every day. In a particular embodiment, the treatment is administered daily, optionally 1, 2 or 3 times a day. In a particular aspect, the treatment is administered is administered at least twice a day, for particularly 2 or 3 times a day. In an alternative aspect, the treatment is administered is administered once a day. The duration of treatment with the compound according to the invention or the pharmaceutical or veterinary composition according to the invention can be weeks, months or even years. In particular, the duration of treatment may last as long as the disease persists.

The amount of compound or pharmaceutical or veterinary composition of the invention to be administered can be determined by standard procedure well known by those of ordinary skill in the art. Physiological data of the patient (e.g. age, size, and weight) and the routes of administration have to be taken into account to determine the appropriate dosage, so as a therapeutically effective amount will be administered to the patient. In a particular aspect, the total compound dose for each administration of the compound or the pharmaceutical or veterinary composition according to the invention is comprised between 0.00001 and 1 g. Optionally, the daily dosage of an L-lysine salt, e.g., in a crystalline form as defined herein, may be varied over a wide range from 10 to 1,000 mg per adult per day, from 25 to 1,000 mg per adult per day, from 50 to 1,000 mg per adult per day, from 25 to 800 mg per adult per day, from 50 to 800 mg per adult per day, from 50 to 600 mg per adult per day or from 100 to 600 mg per adult per day. Preferably, the daily dosage of L-lysine salt or a crystalline form as defined herein is in the range from 25 to 450 mg per day, from 50 to 450 mg per day, from 100 to 450 mg per day, from 150 to 450 mg per day, from 25 to 400 mg per day, from 50 to 400 mg per day, from 100 to 400 mg per day, from 150 to 400 mg per day, from 25 to 350 mg per day, from 50 to 350 mg per day, from 100 to 350 mg per day, from 150 to 350 mg per day, from 200 to 450 mg per day, from 200 to 400 mg per day, from 200 to 350 mg per day, from 250 to 450 mg per day, from 250 to 400 mg per day, or from 250 to 350 mg per day. Optionally, the composition, dosage unit or dosage form contains 5, 10, 15, 25, 50, 75, 100, 200, 300, 400 and 500 mg of an L-lysine salt, e.g., in a crystalline form as defined herein, for the symptomatic adjustment of the dosage to the patient to be treated. A medicament typically contains from about 25 mg to about 800 mg of an L-lysine salt, e.g., in a crystalline form as defined herein, preferably from 25 mg to about 500 mg of an L-lysine salt, e.g., in a crystalline form as defined herein, from 25 mg to about 450 mg of an L-lysine salt, e.g., in a crystalline form as defined herein, from 50 mg to about 400 mg of an L-lysine salt, e.g., in a crystalline form as defined herein, or from 50 mg to about 300 mg of an L-lysine salt, e.g., in a crystalline form as defined herein. This crystalline form may be form I.

The form of the pharmaceutical or veterinary compositions, the route of administration and the dose of administration of the compound or the pharmaceutical or veterinary composition according to the present invention can be adjusted by those skilled in the art according to the type and severity of the disease, and to the patient, in particular its age, weight, sex, and general physical condition.

A further aspect of the invention is an L-lysine salt, e.g., in a crystalline form as defined herein, for use as a drug or a medicine or a pharmaceutical or veterinary composition, which optionally includes a pharmaceutically acceptable carrier or excipient. The invention further relates to the use of an L-lysine salt, e.g., in a crystalline form as defined herein, as a drug or a medicine. The invention further relates to a method for treating a disease in a subject, wherein a therapeutically effective amount of an L-lysine salt, e.g., in a crystalline form as defined herein, is administered to said subject in need thereof. The invention also relates to the use of an L-lysine salt, e.g., in a crystalline form as defined herein, for the manufacture of a medicine. The invention also relates to a pharmaceutical or veterinary composition comprising an L-lysine salt, e.g., in a crystalline form as defined herein, for use as a drug. This crystalline form may be form I.

Optionally, an L-lysine salt, e.g., in a crystalline form as defined herein, or the pharmaceutical or veterinary composition comprising it is for use in the treatment of a disease in combination with an additional therapeutic agent. Optionally, the pharmaceutical or veterinary composition comprising an L-lysine salt, e.g., in a crystalline form as defined herein, further comprises an additional therapeutic agent. Optionally, the present invention relates to a product or kit comprising an L-lysine salt, e.g., in a crystalline form as defined herein, and an additional therapeutic agent as a combined preparation for simultaneous, separate or sequential use, in particular in the treatment of a disease. Optionally, the present invention relates to a combined preparation comprising an L-lysine salt, e.g., in a crystalline form as defined herein, and an additional therapeutic agent for simultaneous, separate or sequential use, in particular in the treatment of a disease. Optionally, the present invention relates to the use of an L-lysine salt, e.g., in a crystalline form as defined herein, or a pharmaceutical or veterinary composition comprising it for the manufacture of a medicine for the treatment of a disease in combination with an additional therapeutic agent. Optionally, the present invention relates to a method for treating a disease in a subject, wherein a therapeutically effective amount of an L-lysine salt, e.g., in a crystalline form as defined herein, and a therapeutically effective amount of an additional therapeutic agent are administered to said subject in need thereof. The additional therapeutic agent to be used in combination with an L-lysine salt, e.g., in a crystalline form as defined herein, can be any of the additional therapeutic agents disclosed below, whatever is the disease to be treated. This crystalline form may be form I.

Optionally, the additional therapeutic agent can be selected from the group consisting of a TLR3 agonist, a TLR7 agonist, a TLR8 agonist, a TLR9 agonist, a RIG-I modulator, a STING agonist, an antiviral agent, such as Bulevirtide, an antibacterial agent, an interferon or a pegylated form thereof, a checkpoint inhibitor such as a PD-1 or PD-L1 agonist, an ERA, an ACE inhibitor, an ARB, a RASS antagonist, a beta-blocker, a diuretic agent, a MRA, a SGLT2 inhibitor, a GLP1 agonist, a SGLT1 inhibitor, FGF19, FGF21, a DPP-4 inhibitor, a PPAR agonist, a THR beta agonist, a FASN, an inhibitor of HSD17b13 or a combination thereof.

The disease to be treated can be selected from the group consisting of a chronic liver disease, a gastrointestinal disease, a renal disease, a cardiovascular disease, a metabolic disease, an infection, a cancer, and an autoimmune disease.

In a first aspect, the disease is an infection, especially a chronic infection. The infection can be a viral infection, a bacterial infection, especially a mycobacterial infection, or a protozoan infection. In a particular aspect, the infection is a viral infection.

The additional therapeutic agent can be any drug useful for the treatment of infection and, for instance, a TLR3 agonist, a TLR7 agonist, a TLR8 agonist, a TLR9 agonist, a RIG-I modulator, a STING agonist, an antiviral agent, such as Bulevirtide, an antibacterial agent, an interferon or a pegylated form thereof, a checkpoint inhibitor such as a PD-1 or PD-L1 agonist, or a combination thereof. In a very particular aspect, the additional therapeutic agent is a TLR3 agonist, such as Poly I:C (polyribosinic:polyribocytidic acid), polyA:U (poly(adenylic acid-uridylic acid), Poly ICLC (polyinosinic acid-polycytidylic acid-poly-L-lysinecarboxy-methylcellulose complex or Hiltonol), PolyI:polyC12U (polyIC12U, Ampligen or Rintatolimod), Riboxxol (RGIC® 50), RIBOXXIM (RGIC® 100), APOXXIM, TL-532, ARNAX, IPH3102, MCT-465 and MCT-485.

A non-exhaustive list of viral infections includes an infection by hepatitis B virus (HBV), hepatitis C virus (HCV), hepatitis D virus (HDV), herpes simplex virus (HSV), papillomavirus (HPV) (e.g., condylomata acuminate), varicella-zoster virus, cytomegalovirus (CMV), rhinoviruses, hepatitis A virus, hepatitis E virus, Kaposis sarcoma herpesvirus, coronavirus including SARS-Cov1, MERS-Cov and SARS-Cov2, retrovirus including HIV, and influenza virus.

In a particular aspect, the viral infection is an infection by hepatitis B virus (HBV), in particular a chronic HBV infection or a chronic HBV hepatitis. Optionally, the additional therapeutic agent to be used in combination for the treatment of HBV is selected from the group consisting of a polymerase inhibitor such as L-nucleosides, deoxyguanosine analogs and nucleoside phosphonates, a nucleoside analog such as lamivudine (Epivir), adefovir (Hepsera), tenofovir (Viread), telbivudine (Tyzeka), entecavir (Baraclude), emtricitabine, and an interferon such as interferon alpha-2a and PEGylated interferon alpha-2a (Pegasys) and interferon alpha-2b (ViraferonPeg ou Introna).

In a particular aspect, the viral infection is an infection by hepatitis D virus (HDV), in particular a chronic HDV infection or a chronic HDV hepatitis.

Optionally, the additional therapeutic agent to be used in combination for the treatment of HDV infection or HBV and HDV co-infection is selected from the group consisting of:
an interferon, for instance an interferon alpha (IFN-α), an interferon lambda or a pegylated form thereof, preferably selected from the group consisting of IFN-α such as IFN-α1a, IFN-α1b, IFN-α2a, IFN-α2b, and IFN-λ such as IFN-λ1a or a pegylated form thereof, more preferably PEG-IFN-α2a (e.g., Pegasys), PEG-IFN-α2b (e.g., ViraferonPeg or Introna) or PEG-IFN-λ1a;
an antiviral agent specific to HDV, for instance a nucleoside analog, a prenylation inhibitor, or a farnesyl transferase inhibitor, preferably ribavirin, ritonavir, lonafarnib and EBP 921, more preferably ritonavir, lonafarnib or a combination thereof;
an antiviral agent specific to HBV, for instance a nucleoside analog such as lamivudine, adefovir, telbivudine, entecavir, tenofovir and emtricitabine;
an antiviral agent specific to HBV and HDV, for instance a nucleoside analog, a nucleic acid polymer, HBsAg secretion inhibitors or a NTCP inhibitor, more preferably bulevirtide (myrcludex B or Hepcludex), ezetimibe, nucleic acid polymer REP 2139 and nucleic acid polymer REP 2165;
a viral expression inhibitor targeting HBV transcripts, in particular a siRNA or an antisense oligonucleotide, for instance JNJ-3989 (ARO-HBV), VIR-2218, RG6346 (DCR-HBVS, RO7445482), Bepirovirsen (GSK3228836, ISIS 505358), or RO7062931;
an antibody against HBV, especially directed against HBsAg, such as VIR-3434; and a combination thereof such as PEG-IFN-λ and lonafarnib, VIR-3434 and VIR-2218, ritonavir and lonafarnib, optionally with PEG-IFN-α2a, JNJ-3989 (ARO-HBV) and entecavir, JNJ-3989 (ARO-HBV) and tenofovir, VIR-2218 and PEG-IFN-α, or bulevirtide and lonafarnib.

In a second aspect, the disease is a renal disease. In a particular aspect, the renal disease comprises renal fibrosis, including glomerulosclerosis and/or tubulointerstitial fibrosis.

In one aspect, the subject to be treated has a renal fibrosis. The renal fibrosis can be diagnosed based on a kidney biopsy. Alternatively, it can be diagnosed based on an alternative analysis such as magnetic resonance imaging (MRI) or urinary tract proteomics (e.g., CKD273).

In a particular aspect, the renal disease is a chronic kidney disease. Preferably, the subject has a renal fibrosis and suffers from a chronic kidney disease.

Chronic Kidney Disease (CKD) is defined as the presence of kidney damage (usually detected as urinary albumin excretion of ≥30 mg/day or equivalent) or decreased kidney function (defined as estimated glomerular filtration rate [eGFR]<60 mL/min/1.73 m2) for three or more months, irrespective of the cause.

In a particular aspect, the CKD is a CKD with a stage chosen from G1, G2, G3a, G3b, G4 or G5, preferably G1, G2, G3a, G3b, or G4, based upon glomerular filtration rate (eGFR) as indicated in Table A, more preferably G2, G3a, G3b, or G4, still more particularly G2, G3a, or G3b. Preferably, the subject has a renal fibrosis.

In another particular aspect, the CKD is a CKD with a CKD stage chosen from A1, A2 or A3 based upon albuminuria (ACR).

TABLE A

Staging of CKD

| Staging | | ACR | | |
|---|---|---|---|---|
| | | A1 | A2 | A3 |
| GFR | G1 | 1* if kidney damage present | 1 | 2 |
| | G2 | 1* if kidney damage present | 1 | 2 |
| | G3a | 1 | 2 | 3 |
| | G3b | 2 | 3 | 3 |
| | G4 | 3 | 4+ | 4+ |
| | G5 | 4+ | 4+ | 4+ |

Optionally, the CKD has a stage selecting from stage 1*, stage 1, stage 2 or stage 3 as defined in Table A. Optionally, the CKD has a stage selecting from stage 1, stage 2 or stage 3 as defined in Table A. Optionally, the CKD has a stage selecting from stage 1 or stage 2 as defined in Table A.

Optionally, the subject has a renal fibrosis or CKD and the disease is selected from the group consisting of hypertension, type 2 diabetes, type 1 diabetes, obesity, Non-Alcoholic Steatohepatitis (NASH), non-alcoholic fatty liver disease (NAFLD), metabolic (dysfunction) associated fatty liver disease (MAFLD), ageing, infectious glomerulonephritis, in particular infections such as syphilis, malaria, hepatitis B, hepatitis C or HIV, focal segmental glomerulosclerosis, IgA nephropathy, minimal change glomerulopathy, membranous nephropathy, renal vasculitis, urinary tract obstruction, genetic alterations, autoimmune diseases such as systemic lupus erythematosus (SLE), and drug- or toxin-induced nephropathy such as nephropathy induced by drugs such as captopril, NSAIDs, penicillamine, probenecid, bucillamine, anti-TNF therapy, and tiopronin or by toxins such as inorganic salts (e.g., gold, mercury), AIDS-associated nephropathy, ischemic nephropathy, tubulointerstitial nephropathy, hepatorenal syndrome, hydronephrosis, renal dysplasia, medullary cystic kidney disease, medullary sponge kidney, multicystic dysplastic kidney, podocytopathy, kidney papillary necrosis, nephritis including glomerulonephritis, hereditary nephritis, interstitial nephritis, pyelitis, nephrocalcinosis, nephrosclerosis, Alport syndrome cystinosis, classical homocystinuria (HCU), Fabry's disease, renal sarcoidosis, diabetic nephropathy, focal segmental glomerulosclerosis (FSGS), hypertensive nephrosclerosis, chronic glomerulonephritis, chronic transplant glomerulopathy, chronic interstitial nephritis, Sjogren's syndrome, Alagille syndrome, alpha 1-antitrypsin deficiency, and polycystic kidney disease.

In a particular aspect, the subject has a renal fibrosis or a CKD and the disease is selected from the group consisting of hypertension, type 2 diabetes, type 1 diabetes, obesity, Non-Alcoholic Steatohepatitis (NASH), non-alcoholic fatty liver disease (NAFLD), metabolic (dysfunction) associated fatty liver disease (MAFLD), ageing, infectious glomerulonephritis, in particular infections such as syphilis, malaria, hepatitis B, hepatitis C or HIV, focal segmental glomerulosclerosis, IgA nephropathy, minimal change glomerulopathy, membranous nephropathy, renal vasculitis, urinary-tract infections, urinary tract obstruction, genetic alterations, autoimmune diseases such as systemic lupus erythematosus (SLE), and drug- or toxin-induced nephropathy such as nephropathy induced by drugs such as captopril, NSAIDs, penicillamine, probenecid, bucillamine, anti-TNF therapy, and tiopronin or by toxins such as inorganic salts (e.g., gold, mercury). Optionally, the subject has a tubulointerstitial fibrosis.

In another particular aspect, the subject has a renal fibrosis or a CKD and the disease is a systemic disease affecting the kidney, for instance a disease selected from the group consisting of hypertension, type 2 diabetes, type 1 diabetes, Non-Alcoholic Steatohepatitis (NASH), non-alcoholic fatty liver disease (NAFLD), metabolic (dysfunction) associated fatty liver disease (MAFLD), infectious glomerulonephritis, in particular infections such as syphilis, malaria, hepatitis B, hepatitis C or HIV, renal vasculitis, autoimmune diseases such as systemic lupus erythematosus (SLE), and drug- or toxin-induced nephropathy such as nephropathy induced by drugs such as captopril, NSAIDs, penicillamine, probenecid, bucillamine, anti-TNF therapy, and tiopronin or by toxins such as inorganic salts (e.g., gold, mercury). Optionally, the subject has a tubulointerstitial fibrosis.

Optionally, the subject suffers from type 2 diabetes or type 1 diabetes. The subject may have a CKD of stage 1, 2 or 3 as defined above in Table A. Optionally, the subject has a renal fibrosis, especially a tubulointerstitial fibrosis.

Optionally, the subject suffers from systemic lupus erythematosus (SLE). The subject may have a CKD of stage 1, 2 or 3 as defined above in Table A. In this context, the subject may have a lupus nephropathy of class III, IV, V or VI. Optionally, the subject has a renal fibrosis, especially a tubulointerstitial fibrosis.

Optionally, the subject suffers from NASH or NAFLD. The subject may have a CKD of stage 1, 2 or 3 as defined above defined in Table A. Non-alcoholic steatohepatitis (NASH) is a disease characterized by excessive fat accumulation, inflammation, and ballooning degeneration of hepatocytes, with or without fibrosis in the liver. In addition, some subjects affected by NASH may further present chronic kidney disease. For these particular subjects, the compounds of the invention could be of particular interest. Indeed, the compounds of the invention are able to decrease significantly the inflammation and fibrosis in a dose-dependent manner in the liver and they are further capable of significantly inhibiting fibrosis in the kidney and even reversing the existing fibrosis and also of decreasing renal inflammation. Accordingly, the compounds of the present invention could be useful for protecting a subject suffering from NASH of liver and renal lesions or for treating a subject suffering from NASH so as to limit, slow down or reverse liver and renal lesions. Then, the subject is in particular a subject suffering from NASH or NAFLD and having a renal fibrosis. Optionally, the subject is a subject suffering from NASH or NAFLD and from CKD. Optionally, the subject has a renal fibrosis, especially a tubulointerstitial fibrosis.

Optionally, the renal disease is selected from the group consisting of AIDS-associated nephropathy, ischemic nephropathy, tubulointerstitial nephropathy, hepatorenal syndrome, hydronephrosis, renal dysplasia, medullary cystic kidney disease, medullary sponge kidney, multicystic dysplastic kidney, podocytopathy, kidney papillary necrosis, nephritis including glomerulonephritis, hereditary nephritis, interstitial nephritis, pyelitis, nephrocalcinosis, nephrosclerosis, Alport syndrome cystinosis, classical homocystinuria (HCU), Fabry's disease, renal sarcoidosis, diabetic nephropathy, focal segmental glomerulosclerosis (FSGS), hypertensive nephrosclerosis, chronic glomerulonephritis, chronic transplant glomerulopathy, chronic interstitial nephritis, Sjogren's syndrome, Alagille syndrome, alpha 1-antitrypsin deficiency, and polycystic kidney disease.

Optionally, the renal disease is selected from the group consisting of AIDS-associated nephropathy, ischemic nephropathy, tubulointerstitial nephropathy, hepatorenal syndrome, hydronephrosis, renal dysplasia, medullary cystic kidney disease, medullary sponge kidney, multicystic dysplastic kidney, podocytopathy, kidney papillary necrosis, nephritis including glomerulonephritis, hereditary nephritis, interstitial nephritis, pyelitis, nephrocalcinosis, nephrosclerosis, Alport syndrome cystinosis, classical homocystinuria (HCU), Fabry's disease and renal sarcoidosis.

Optionally, the renal disease is selected from the group consisting of diabetic nephropathy, focal segmental glomerulosclerosis (FSGS), hypertensive nephrosclerosis, chronic glomerulonephritis, chronic transplant glomerulopathy, chronic interstitial nephritis, Sjogren's syndrome, Alagille syndrome, alpha 1-antitrypsin deficiency, and polycystic kidney disease.

The effect of the L-lysine salt or a crystalline form as defined herein on the disease can be for instance assessed by the measure of eGFR or ACR. A therapeutic effect could be the improvement of eGFR and/or ACR. The therapeutic effect could be the stabilization of eGFR and/or ACR. The therapeutic effect could also be a delay of the progression of the disease or a slow-down of the progression of the disease, for instance as assessed by eGFR and/or ACR assays.

Optionally and non-exhaustively, the additional therapeutic agent to be used in combination for the treatment of renal disease is selected from the group consisting of:
an endothelin receptor antagonist (ERA), for instance selected from the group consisting of bosentan, macitentan, tezosentan, sitaxentan, ambrisentan, atrasentan, BQ-123, zibotentan, edonentan, A192621 (CAS No 195529-54-5) and BQ-788 (CAS No 156161-89-6);
an ACE inhibitor (Angiotensin-Converting Enzyme), for instance selected from the group consisting of benazepril, captopril, enalapril, fosinopril, lisinopril, moexipril, perindopril, quinapril, ramipril and trandolapril;
an ARB (Angiotensin II Receptor Blocker), for instance selected from the group consisting of losartan, candesartan, valsartan, irbesartan, telmisartan, eprosartan, Olmesartan, azilsartan, and fimasartan;
a RASS (renin-angiotensin-aldosterone system) antagonist, for instance selected from the group consisting of captopril, imidapril, zofenopril, candesartan, delapril, telmisartan, aliskiren, moexipril, enalapril, valsartan, fosinopril, irbesartan, perindopril, quinapril, ramipril, eprosartan, Olmesartan, trandolapril, losartan, azilsartan, lisinopril, spirapril, benazepril, and cilazapril;
a Beta-blocker (beta-adrenoceptor-blocker), for instance selected from the group consisting of metoprolol, atenolol, bisoprolol, nebivolol, propranolol, nadolol, carvedilol, labetalol, and timolol;
a diuretic agent, for instance selected from the group consisting of furosemide, azosemide, bumetanide, piretanide, torasemide ethacrynic acid (torasemide), and etozolin;
a MRA (Mineralocorticoid Receptor Antagonist or Aldosterone Receptor Antagonist), for instance selected from the group consisting of spironolactone, eplerenone, canrenone, finerenone and mexrenone;
a SGLT2 (sodium-glucose linked transporter 2) protein inhibitor, also called gliflozin, for instance selected from the group consisting of bexagliflozin, canagliflozin, dapagliflozin, empagliflozin, ertugliflozin, ipragliflozin, luseogliflozin, remogliflozin, sergliflozin, sotagliflozin and tofogliflozin;
a GLP1 agonist (Glucagon-like peptide-1 receptor agonist), for instance selected from the group consisting of exenatide, liraglutide, albiglutide, dulaglutide, lixisenatide, semaglutide and tirzepatide;
ELX-02 (CAS No.: 1375073-95-2); and
Pegtibatinase (CAS No.: 2304692-47-3).

More particularly, the additional therapeutic agent to be used in combination for the treatment of CKD or renal fibrosis is selected from the groups as detailed above comprising ERA, ACE inhibitors, ARB, RASS antagonists, beta-blockers, diuretic agents, MRA, SGLT2 inhibitors, GLP1 agonists and any combination thereof.

More particularly, the additional therapeutic agent to be used in combination for the treatment of genetic renal diseases such as Alport syndrome cystinosis is ELX-02 (CAS No.: 1375073-95-2).

More particularly, the additional therapeutic agent to be used in combination for the treatment of HCU is Pegtibatinase (CAS No.: 2304692-47-3).

In a third aspect, the disease is a liver disease, especially a chronic liver disease. The chronic liver disease can be selected from the group consisting of primary biliary cirrhosis or primary biliary cholangitis (PBC), cerebrotendinous xanthomatosis (CTX), primary sclerosing cholangitis (PSC), drug induced cholestasis, intrahepatic cholestasis of pregnancy, parenteral nutrition associated cholestasis (PNAC), bacterial overgrowth or sepsis associated cholestasis, autoimmune hepatitis, chronic viral hepatitis, alcoholic liver disease, nonalcoholic fatty liver disease (NAFLD), nonalcoholic steatohepatitis (NASH), alcoholic hepatitis, liver transplant associated graft versus host disease, living donor transplant liver regeneration, congenital hepatic fibrosis, choledocholithiasis, granulomatous liver disease, intra- or extrahepatic malignancy, Sjogren's syndrome, Alagille syndrome, Sarcoidosis, Wilson's disease, Gaucher's disease, hemochromatosis, biliary atresia, ductopenic liver transplant rejection, cystic fibrosis liver disease and alpha 1-antitrypsin deficiency. In a very particular aspect, the disease is NASH.

Optionally, the additional therapeutic agent to be used in combination for the treatment of a liver disease, especially of a subject suffering from NASH, can be:

- a SGLT2 (sodium-glucose linked transporter 2) protein inhibitor, also called gliflozin, for instance selected from the group consisting of bexagliflozin, canagliflozin, dapagliflozin, empagliflozin, ertugliflozin, ipragliflozin, luseogliflozin, remogliflozin, sergliflozin, sotagliflozin and tofogliflozin;
- a GLP1 agonist (Glucagon-like peptide-1 receptor agonist), for instance selected from the group consisting of exenatide, liraglutide, albiglutide, dulaglutide, lixisenatide, semaglutide and tirzepatide;
- FGF19 (Fibroblast Growth Factor 19);
- FGF21 (Fibroblast Growth Factor 21);
- a DPP-4 inhibitor (dipeptidyl peptidase 4), for instance selected from the group consisting of sitagliptin, vildagliptin, saxagliptin, linagliptin, gemigliptin, anagliptin, teneligliptin, alogliptin, trelagliptin, omarigliptin, evogliptin and gosogliptin;
- a PPAR agonist, for instance selected from the group consisting of Naveglitazar, elafibranor, lanifibranor, saroglitazar, and pioglitazone;
- a SGLT1 (sodium-glucose linked transporter) inhibitor, for instance selected from the group consisting of sotagliflozin, licogliflozin, and mizagliflozin;
- a THR (Thyroid Hormone Receptor) beta agonist such as resmetirom;
- a FASN (Fatty Acid Synthase) inhibitor such as orlistat; or
- an inhibitor of HSD17b13 (hydroxysteroid 17β-dehydrogenase 13), especially an oligonucleotide decreasing its expression such as a siRNA or an antisense oligonucleotide or an antibody (US-2019106749, the disclosure thereof being incorporated herein by reference).

In a fourth aspect, the disease is an autoimmune or inflammatory disease. For instance, the disease can be selected in the group consisting of multiple sclerosis, rheumatoid arthritis, Behçet's syndrome, Churg-Strauss syndrome, Guillain-Barre syndrome, Bile acid diarrhea (BAD), inflammatory bowel disease (IBD) including ulcerative colitis and Crohn's disease, and irritable bowel syndrome (IBS), especially Bile acid diarrhea (BAD), inflammatory bowel disease (IBD) including ulcerative colitis and Crohn's disease, and irritable bowel syndrome (IBS).

In an additional aspect, the disease is a cardiovascular disease, for instance selected from the group consisting of insulin resistance, Type I and Type II diabetes, and obesity.

In an additional aspect, the disease is a cancer. For instance, the cancer can be a solid cancer or a hematopoietic cancer, preferably chosen among AIDS-related Kaposi's sarcoma, leukemia such as hairy-cell leukemia, chronic myeloid leukemia and non-Hodgkin's leukemia, lymphoma such as follicular lymphoma, cutaneous T-cell lymphoma and adult T-cell leukemia-lymphoma, carcinoid tumors, melanoma, multiple myeloma, renal cell carcinoma, colorectal adenocarcinoma, hepatocarcinoma, breast cancer, prostate cancer, ovarian cancer, pancreas cancer, peritoneal cancer, bladder cancer, lung cancer, glioblastoma, oral carcinoma, glioma, head and neck cancer, sarcoma, and neuroendocrine tumors. The additional therapeutic agent can be any drug useful for the treatment of a cancer, non-exhaustively, a chemotherapy including an inhibitor of topoisomerases I or II, a DNA crosslinker, a DNA alkylating agent, an anti-metabolic agent and inhibitors of the mitotic spindles, radiotherapy, hormonal therapy, targeted therapy, for instance with HDAC inhibitors, PARP inhibitors, kinase inhibitors (e.g., inhibitors of EGFR, ALK, KRAS), antiangiogenic agents, hypomethylating agents, cancer vaccines, checkpoints inhibitors, immunotherapies, a T-cell-based cancer immunotherapy including adoptive cell transfer (ACT), genetically modified T-cells or engineered T-cells such as chimeric antigen receptor cells (CAR-T cells), and an antibody drug conjugate.

In an additional aspect, the disease can be selected from the group consisting of age-related macular degeneration, angiomatous disease, thrombocythemia, polycythemia vera, agnogenic myeloid metaplasia, leishmaniasis, osteoporosis, and Chronic fatigue syndrome.

Further aspects and advantages of the present invention will be described in the following examples, which should be regarded as illustrative and not limiting.

EXAMPLES

Example 1: Synthesis of EYP001 L-Lysine Salt

1. Synthesis
Sample A:
To a solution of 400 mg of EYP001 solubilized in THF (10 mL) was added a quantity of L-lysine (solubilized in EtOH/H$_2$O 2/1 mL) corresponding to a 1:1 stoichiometry.

After a few minutes of stirring at room temperature for homogenization, a strong crystallization occurred.

Several cycles (3) of heating (30 min at 40° C.) and cooling (30 min at room temperature) were then performed to potentially increase the size and quality of the crystals.

The solvents were then removed by filtration, and the crystals were washed twice with the recovered saturated filtrate before being finally further dried under vacuum at 60° C. for about 1 h.
Sample B—Scale Up Production
To a solution of 4 g of EYP001 solubilized in THF (50 mL) was added a quantity of L-lysine (solubilized in EtOH/H$_2$O 1:1) corresponding to a 1:1 stoichiometry.

After a few minutes of stirring at room temperature for homogenization, a strong crystallization occurred.

Several cycles (2) of heating (30 min at 40° C.) and cooling (30 min at room temperature) were then performed to potentially increase the size and quality of the crystals.

The solvents were then removed by filtration, and the crystals were washed twice with the recovered saturated filtrate before being finally further dried under vacuum at 60° C. for about 4 h.

Higher scale batches were further produced starting from 65.05 g and 337.6 g of EYP001 with 93.1% and 97.3% yields, respectively.

2. Analysis of the Product
X-Ray Powder Diffraction (XRPD)

X-ray diffraction (XRD) analysis was performed on a Brüker D2 Phaser diffractometer, using a copper anti-cathode, a mono-crystalline silicon sample holder and a Lynx-Eye linear detector. Instrument operating conditions for X-ray pattern acquisition were as follows:

|  | Temperature | Ambient |
|---|---|---|
|  | Atmosphere | Ambient |
| X-ray generator | voltage (kV) | 30 |
|  | intensity (mA) | 10 |

| X-ray source | target | Cu |
|---|---|---|
| | emission radiation Kα (nm) | 0.154184 |
| | Kβ filter radiation | Nickel |
| Slit | anti-divergence (mm) | 1 |
| | sollers slit (°) | 2.5 |
| Goniometer | angular sector analyzed (° for 2θ) | 4-40, 0-50 or 4-50 |
| | step size (° for 2θ) | 0.07 |
| | Sample holder rotation speed (rpm) | 30 |
| Detection | exposition time per step size of goniometer (s) | 1 or 3 |

Powder samples were loaded onto a flat mono-crystalline silicon sample holder in a way to avoid preferred orientation (not randomly oriented particles) and to ensure planarity of the specimen surface.

FIG. 1 presents the XRPD pattern of EYP001 L-lysine salt (Sample A), L-lysine counter-ion, and EYP001. A visual comparison of these patterns clearly shows that a new crystallised form was isolated (form I). The following table 1 discloses the list of XRPD pics corresponding to the spectrum of FIG. 3A.

TABLE 1

| Angle 2-Thêta (°) | Inter-reticular distance (Å) | Intensity c.p.s. | % |
|---|---|---|---|
| 5.2 | 17.1 | 2621 | 12.8 |
| 7.6 | 11.7 | 7592 | 37.2 |
| 8.6 | 10.2 | 472 | 2.3 |
| 9.1 | 9.7 | 563 | 2.8 |
| 10.1 | 8.8 | 13162 | 64.5 |
| 11.6 | 7.6 | 3002 | 14.7 |
| 12.6 | 7.0 | 15458 | 75.7 |
| 13.7 | 6.5 | 1636 | 8.0 |
| 14.2 | 6.3 | 1200 | 5.9 |
| 14.4 | 6.1 | 1447 | 7.1 |
| 15.1 | 5.9 | 20420 | 100.0 |
| 15.9 | 5.6 | 714 | 3.5 |
| 16.3 | 5.4 | 2179 | 10.7 |
| 16.6 | 5.3 | 454 | 2.2 |
| 17.1 | 5.2 | 2009 | 9.8 |
| 17.6 | 5.0 | 16409 | 80.4 |
| 18.4 | 4.8 | 801 | 3.9 |
| 18.8 | 4.7 | 1255 | 6.1 |
| 19.2 | 4.6 | 1586 | 7.8 |
| 20.1 | 4.4 | 9957 | 48.8 |
| 20.5 | 4.3 | 1145 | 5.6 |
| 20.9 | 4.2 | 3149 | 15.4 |
| 21.7 | 4.1 | 948 | 4.6 |
| 22.1 | 4.0 | 1717 | 8.4 |
| 23.3 | 3.8 | 3652 | 17.9 |
| 24.0 | 3.7 | 2548 | 12.5 |
| 24.5 | 3.6 | 1778 | 8.7 |
| 24.8 | 3.6 | 971 | 4.8 |
| 25.1 | 3.5 | 1029 | 5.0 |
| 25.9 | 3.4 | 2887 | 14.1 |
| 26.7 | 3.3 | 624 | 3.1 |
| 27.8 | 3.2 | 3360 | 16.5 |
| 28.4 | 3.1 | 641 | 3.1 |
| 28.7 | 3.1 | 1184 | 5.8 |
| 29.0 | 3.1 | 713 | 3.5 |
| 29.3 | 3.0 | 1928 | 9.4 |
| 30.3 | 2.9 | 4176 | 20.5 |
| 30.9 | 2.9 | 447 | 2.2 |
| 31.2 | 2.9 | 506 | 2.5 |
| 31.6 | 2.8 | 459 | 2.2 |
| 32.7 | 2.7 | 336 | 1.6 |
| 33.2 | 2.7 | 466 | 2.3 |
| 33.7 | 2.7 | 372 | 1.8 |
| 34.1 | 2.6 | 538 | 2.6 |
| 34.9 | 2.6 | 413 | 2.0 |
| 35.5 | 2.5 | 2284 | 11.2 |
| 36.3 | 2.5 | 688 | 3.4 |
| 36.6 | 2.5 | 460 | 2.3 |
| 36.9 | 2.4 | 362 | 1.8 |
| 37.4 | 2.4 | 346 | 1.7 |
| 38.1 | 2.4 | 1043 | 5.1 |
| 38.8 | 2.3 | 391 | 1.9 |
| 40.5 | 2.2 | 514 | 2.5 |
| 40.9 | 2.2 | 315 | 1.5 |
| 41.3 | 2.2 | 369 | 1.8 |
| 42.5 | 2.1 | 335 | 1.6 |
| 43.0 | 2.1 | 342 | 1.7 |
| 43.5 | 2.1 | 315 | 1.5 |
| 43.7 | 2.1 | 489 | 2.4 |
| 44.9 | 2.0 | 364 | 1.8 |
| 45.3 | 2.0 | 304 | 1.5 |
| 45.6 | 2.0 | 310 | 1.5 |
| 46.1 | 2.0 | 337 | 1.7 |
| 47.7 | 1.9 | 327 | 1.6 |
| 48.5 | 1.9 | 251 | 1.2 |
| 48.9 | 1.9 | 266 | 1.3 |
| 49.2 | 1.9 | 276 | 1.4 |

Figure 2:
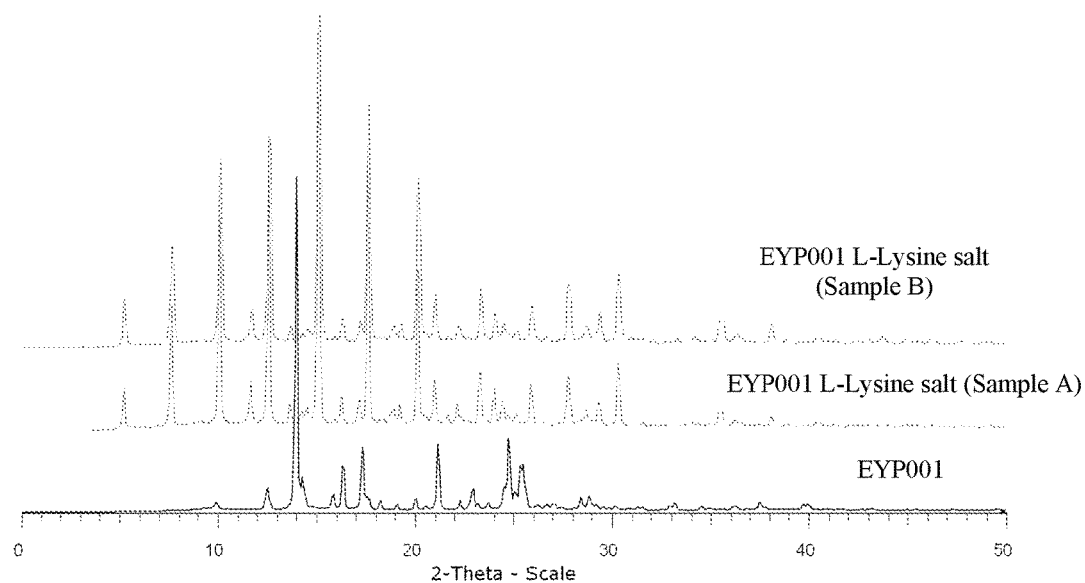
FIG. 2: Overlaid XRPD profiles of EYP001 L-lysine salt (sample B), EYP001 L-lysine salt (sample A), and EYP001 acid form.
Figure 3B:
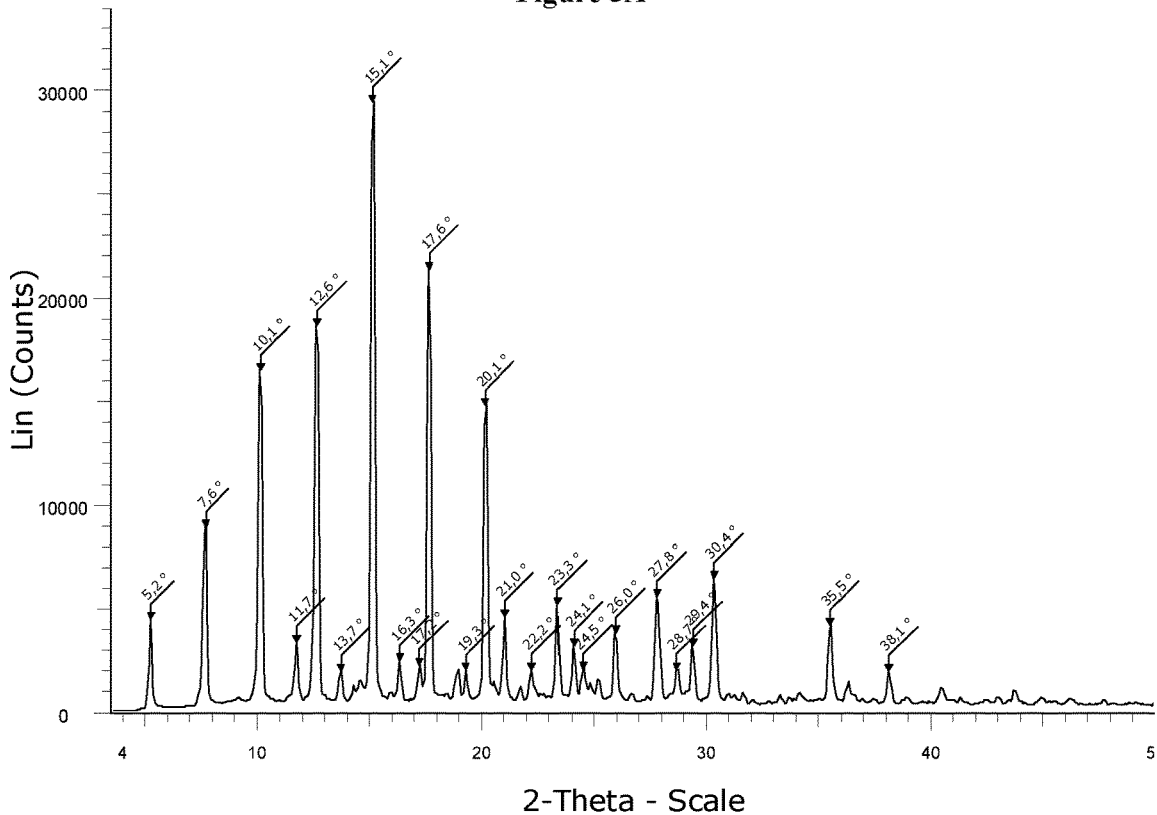

FIG. 2 presents the XRPD pattern of EYP001 L-lysine salt (Sample B), EYP001 L-lysine salt (Sample A), and EYP001. A visual comparison of these patterns clearly shows a correspondence for the two samples A and B, indicating thereby that Sample B had crystallised into the same crystal form as Sample A. The following table 2 discloses the list of XRPD pics corresponding to the spectrum of FIG. 3B.

TABLE 2

| Angle 2-Thêta (°) | Inter-reticular distance (Å) | Intensity c.p.s. | % |
|---|---|---|---|
| 5.2 | 17.0 | 4470 | 15.2 |
| 7.7 | 11.5 | 8895 | 30.2 |
| 9.1 | 9.7 | 663 | 2.3 |
| 10.1 | 8.7 | 16497 | 56.0 |
| 11.3 | 7.8 | 761 | 2.6 |
| 11.7 | 7.6 | 3361 | 11.4 |
| 12.6 | 7.0 | 18661 | 63.4 |
| 13.7 | 6.5 | 1948 | 6.6 |
| 14.3 | 6.2 | 1238 | 4.2 |
| 14.5 | 6.1 | 1517 | 5.2 |
| 15.1 | 5.9 | 29456 | 100.0 |
| 15.9 | 5.6 | 923 | 3.1 |
| 16.3 | 5.4 | 2448 | 8.3 |
| 17.2 | 5.2 | 2251 | 7.6 |
| 17.6 | 5.0 | 21380 | 72.6 |
| 18.4 | 4.8 | 849 | 2.9 |
| 18.9 | 4.7 | 2032 | 6.9 |
| 19.3 | 4.6 | 2004 | 6.8 |
| 20.1 | 4.4 | 14786 | 50.2 |
| 20.6 | 4.3 | 1413 | 4.8 |
| 21.0 | 4.2 | 4608 | 15.6 |
| 21.7 | 4.1 | 1177 | 4.0 |
| 22.2 | 4.0 | 2020 | 6.9 |
| 23.3 | 3.8 | 5180 | 17.6 |
| 24.1 | 3.7 | 3173 | 10.8 |
| 24.5 | 3.6 | 2052 | 7.0 |
| 24.9 | 3.6 | 1399 | 4.7 |
| 25.2 | 3.5 | 1572 | 5.3 |
| 26.0 | 3.4 | 3812 | 12.9 |
| 26.7 | 3.3 | 871 | 3.0 |
| 27.4 | 3.3 | 741 | 2.5 |
| 27.8 | 3.2 | 5567 | 18.9 |
| 28.4 | 3.1 | 841 | 2.9 |
| 28.7 | 3.1 | 2027 | 6.9 |
| 29.4 | 3.0 | 3197 | 10.9 |
| 30.4 | 2.9 | 6448 | 21.9 |
| 31.0 | 2.9 | 856 | 2.9 |
| 31.3 | 2.9 | 768 | 2.6 |

TABLE 2-continued

| Angle 2-Thêta (°) | Inter-reticular distance (Å) | Intensity c.p.s. | % |
|---|---|---|---|
| 31.6 | 2.8 | 884 | 3.0 |
| 32.1 | 2.8 | 570 | 1.9 |
| 33.3 | 2.7 | 789 | 2.7 |
| 33.8 | 2.7 | 666 | 2.3 |
| 34.1 | 2.6 | 879 | 3.0 |
| 35.5 | 2.5 | 4180 | 14.2 |
| 36.3 | 2.5 | 1415 | 4.8 |
| 36.9 | 2.4 | 588 | 2.0 |
| 37.5 | 2.4 | 605 | 2.1 |
| 38.1 | 2.4 | 1964 | 6.7 |
| 38.9 | 2.3 | 651 | 2.2 |
| 39.7 | 2.3 | 478 | 1.6 |
| 40.5 | 2.2 | 1169 | 4.0 |
| 41.0 | 2.2 | 557 | 1.9 |
| 41.3 | 2.2 | 646 | 2.2 |
| 42.5 | 2.1 | 577 | 2.0 |
| 43.0 | 2.1 | 672 | 2.3 |
| 43.5 | 2.1 | 556 | 1.9 |
| 43.7 | 2.1 | 1015 | 3.4 |
| 45.0 | 2.0 | 645 | 2.2 |
| 45.6 | 2.0 | 511 | 1.7 |
| 46.2 | 2.0 | 632 | 2.1 |
| 47.8 | 1.9 | 540 | 1.8 |

Differential Scanning Calorimetry (DSC)

Differential scanning calorimeter (DSC) analysis was performed on a Q2000 TA Instruments analyser. The sample to be analysed was weighed in an aluminium capsule, which was then crimped and put into the calorimeter oven.

Instrument operating conditions for DSC profile acquisition were as follows:

| Heater ramp (° C./min) | 10 |
|---|---|
| Final temperature (° C.) | 300° C. |
| Carrier gas       nitrogen | Messer, "qualité Azote 5.0" |
| flow rate (mL/min) | 50 |

Figure 4:
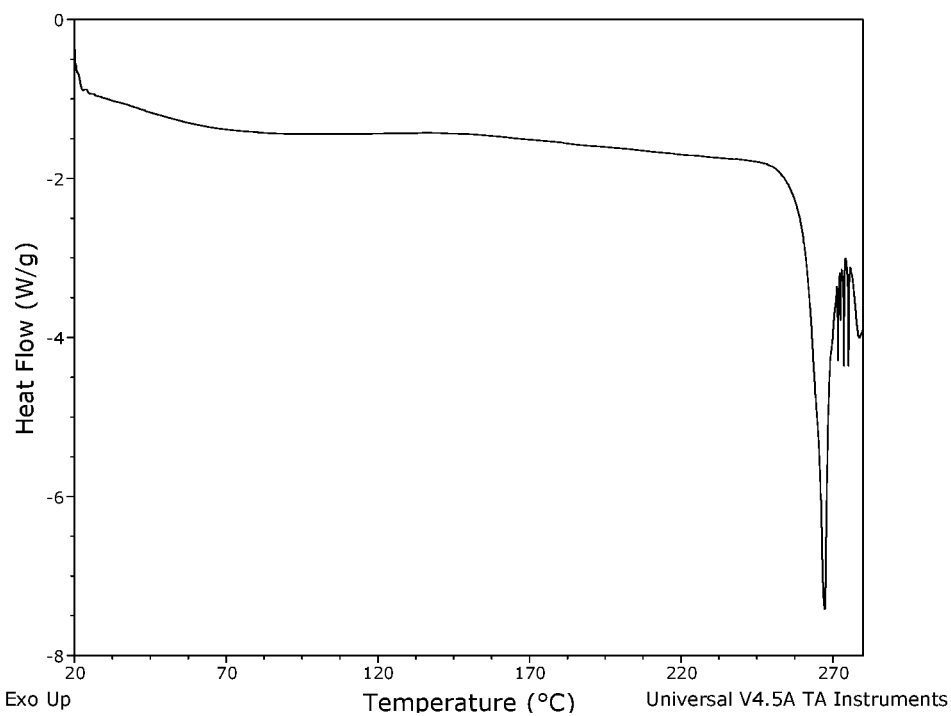
FIG. 4: DSC profile of EYP001 L-lysine salt (sample A).

The DSC profile of the EYP001 L-lysine salt (sample A) as well as the DSC detailed integration results are presented in FIG. 4 and Table 3, respectively.

Upon heating, one strong endotherm (with an onset temperature of 264° C.) can be observed right before (or at the beginning of) the main thermal decomposition of the compound, and can be associated to the melting of the EYP001 L-lysine salt.

TABLE 3

Quantitative DSC results of EYP001 L-lysine salt (sample A)

| Event | Transition | Temperature (° C.) Onset | Peak | Transition enthalpy (J/g) |
|---|---|---|---|---|
| 1 | Strong endotherm | 264 | 267 | −117 |

Thermogravimetry (TGA)

Thermogravimetric analysis was performed on a TA Instruments TGA Hi-Res 2950 apparatus equipped with an evolved gas analysis furnace. A sample was placed in an opened aluminium basket and analysed according to the following conditions:

| Mass assay (mg) | # 5 |
|---|---|
| Heater ramp (° C./min) | 10 |
| Final temperature (° C.) | 500° C. |
| Carrier gas       nitrogen | Messer, "qualité Azote 5.0" |
| flow rate (mL/min) | 95-105 |

Figure 5:
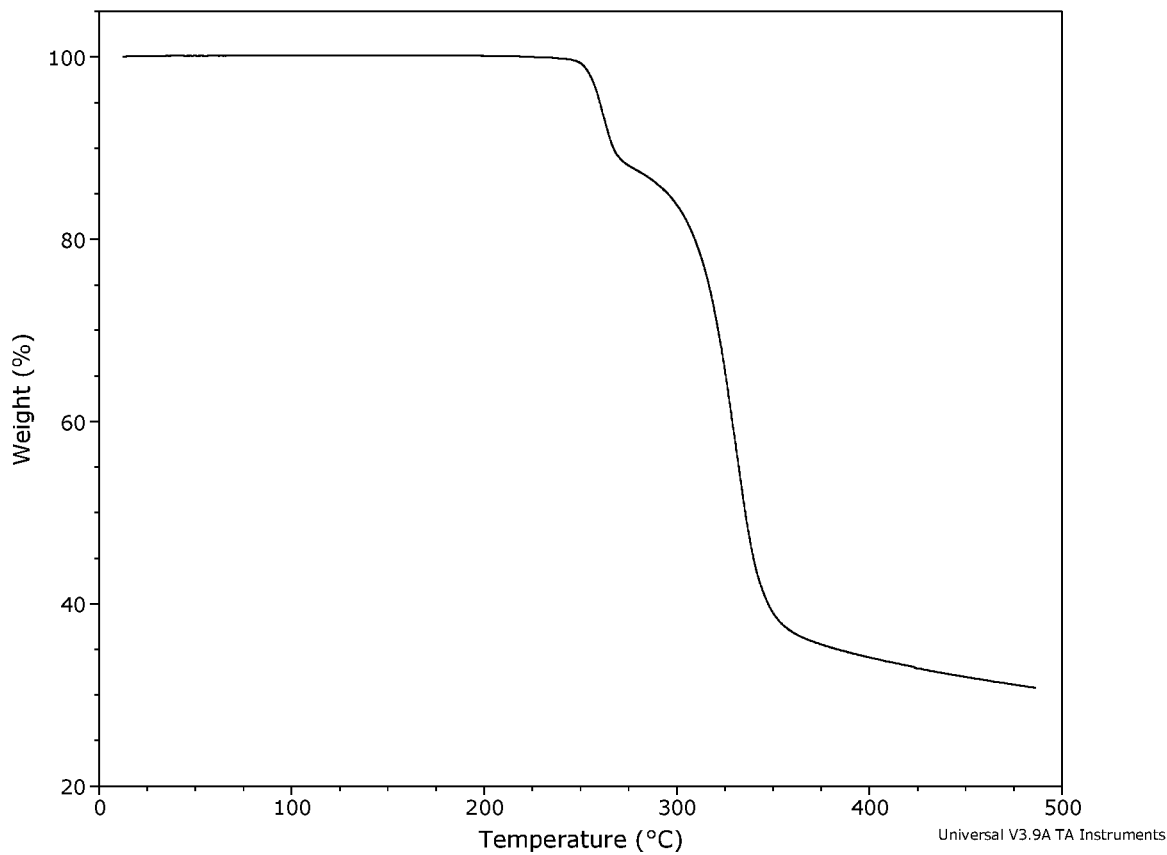
FIG. 5: TGA profile of EYP001 L-lysine salt (sample A).

TGA profile of the EYP001 L-lysine salt (sample A) and TGA detailed integration results are presented in FIG. 5 and Table 4, respectively. Upon heating, no mass loss was detected before the beginning of the thermal decomposition of the compound (observed with an onset temperature of 254° C.).

TABLE 4

Quantitative TGA results of EYP001 L-lysine salt (sample A)

Mass losses upon heating

| Step | Δm (%) | Start (° C.) | $T_{Onset}$ (° C.) | $T_{Endset}$ (° C.) | Stop (° C.) |
|---|---|---|---|---|---|
| 1 | 12.8 | 190 | 254 | 267 | 280 |
| 2 | 57.2 | 280 | 315 | 345 | 486 |

Dynamic Vapor Sorption (DVS)

The dynamic vapor sorption (DVS) analysis (gas water sorption) was performed on a DVS-Intrinsic incubator (SMS Ltd), equipped with DVS-Intrinsic Control Software 1.0. The sample, placed in an aluminium basket holder, was submitted to a full-cycle analysis (sorption followed by desorption cycle) under the following conditions:

| Temperature | 25° C. |
|---|---|
| Carrier gas and rate | dried and filtered air at 200 mL · min$^{-1}$ |
| Mode and criterion | dm/dt ≤0.002% · min$^{-1}$ |
| Humidity range | 0 to 95% RH |
| RH step | 5% |
| Minimum step time | 10 minutes |
| Maximum step time | 360 minutes |

The sample was first pre-dried under a stream of dry air until a stabilized sample mass was observed. Then, the relative humidity was increased by 5% increments. At each step, the sample mass was allowed to increase until equilibrium is reached (according to a given dm/dt target), and then a new relative humidity rise occurred. Relative humidity was ramped up to 95%. After equilibration at this point, desorption began in a similar stepwise manner, with sample mass decrease again allowed to stabilize after each incremental humidity decrease.

With both segments of the above-described method, the sample mass recording allowed describing of the whole vapor water sorption/desorption behaviour versus relative humidity.

The sample EYP001 L-lysine salt (Sample A) was first dried (maintained at 0% RH) before being submitted to the sorption-desorption cycle. During the preliminary drying phase (sample maintained at 25° C./0% RH before starting the vapor water sorption process), no significant mass loss was observed.

Figure 6:
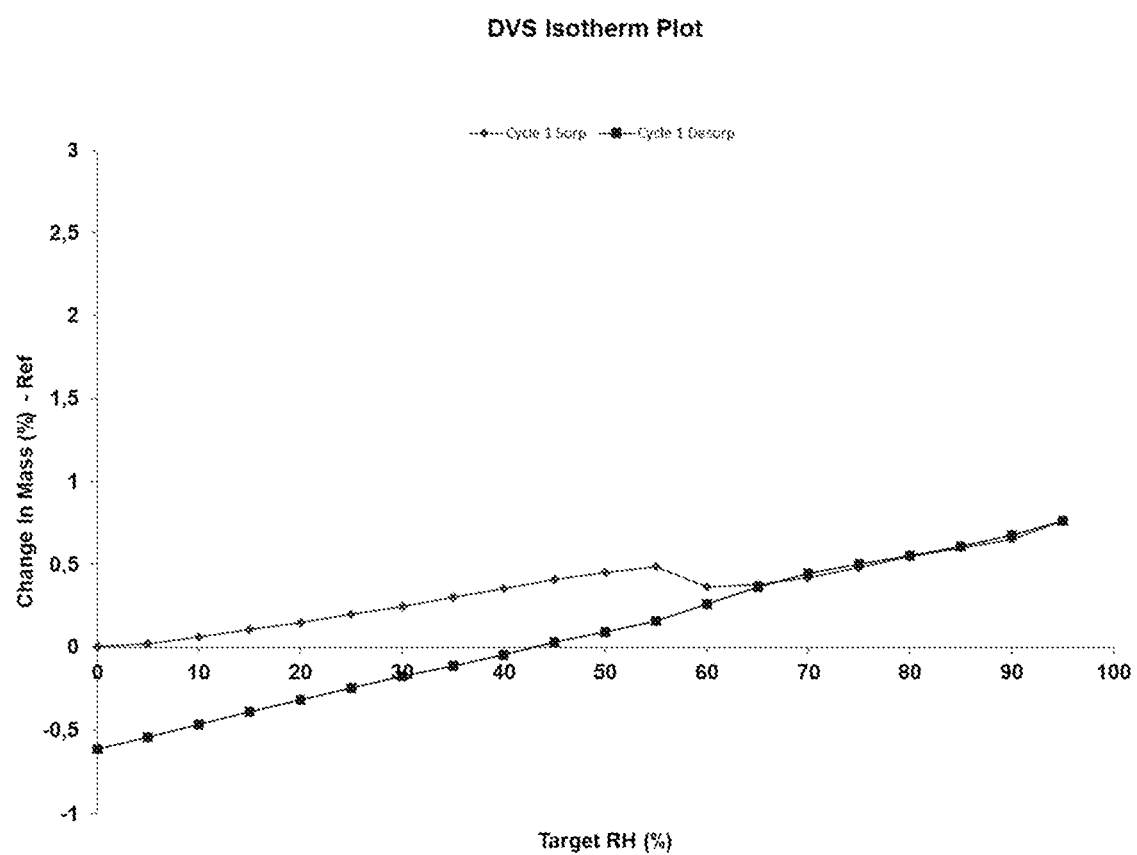
FIG. 6: DVS isotherm sorption plot at 25° C. of EYP001 L-lysine salt (sample A).

FIG. 6 displays the recorded DVS isotherm plot (water sorption/desorption traces) of the tested sample.

Upon sorption, the sample adsorbed water regularly up to 0.8% at 25° C./95% RH. The slight decrease in mass observed between 55 and 60% RH could be attributed to an insignificant structure reorganisation upon water uptake.

The desorption process evidenced a linear and regular loss of the adsorbed water.

When coming back to 0% RH after a full sorption-desorption cycle, the final sample mass was roughly the same as the initial one (beginning of the first 25° C./0% RH step).

With only 0.4% water uptake at 60% RH, the studied bulk can be considered as being clearly non-hygroscopic (API bulks are usually said to start being hygroscopic above 2% mass gain at 25° C./60% RH).

Polymorph Screening

Amorphous EYP001 L-Lysine Salt

The amorphous material was generated by melt quench experiments. Around 10-30 mg of EYP001 L-lysine salt (form I) were added to a HPLC vial and flushed with nitrogen ($N_2$) to prevent degradation. This vial was heated to 200-250° C. maximum (degradation occurring concomitantly with melting around 265° C.) for around 2 minutes to melt the solid and then quickly immersed it in ice or in liquid $N_2$ to form X-ray amorphous EYP001 L-lysine salt.

The amorphous material was also prepared by freeze drying of EYP001 L-lysine salt (form I). This amorphous material was found stable over at least 19 days under ambient conditions.

Screening Experiments

A polymorph screening was performed on EYP001 L-lysine salt crystalline form I (form I as starting material unless otherwise specified).

A number of unique materials with different patterns were produced, including crystalline forms I-IV and an amorphous material. All solids from the screening experiments were analysed by XRPD analysis and the resulting patterns compared to that of the reference. The observed solids and their ways of obtention are described in Table 5.

TABLE 5

| Entry | Solvent | Anti-solvent | Screen method | Results | XRPD |
|---|---|---|---|---|---|
| 1 | none | none | 23% RH stress | solid | Form I |
| 2 | none | none | 40° C./75% RH stress | solid | Form I |
| 3 | none | none | 59% RH stress | solid | Form I |
| 4* | none | none | 23% RH stress | solid | Amorphous |
| 5* | none | none | 40° C./75% RH stress | solid | Form I |
| 6* | none | none | 59% RH stress | solid | Form I |
| 7 | none | none | melt quench | solid | Amorphous |
| 8 | none | none | compression | solid | Form I |
| 9* | none | none | milling | solid | Amorphous |
| 10 | none | none | milling | solid | Amorphous |
| 11* | THF | none | flash evaporation | solid | Amorphous |
| 12 | THF | none | slurry (50° C.) | solid | Amorphous |
| 13 | DMSO | none | slurry (20° C.) | solid | Form I |
| 14 | EtOAc | none | slurry (5° C.) | solid | Form I |
| 15 | water | none | slurry (5° C.) | solid | Form III |
| 16 | THF | none | flash evaporation | no solid | Amorphous |
| 17 | THF | none | flash evaporation | solid | Form II |
| 18 | acetone | none | flash evaporation | solid | Amorphous |
| 19 | DMSO | none | flash evaporation | solid | Form I |
| 20 | EtOAc | none | flash evaporation | solid | Amorphous |
| 21 | IPA | none | flash evaporation | solid | Amorphous |
| 22 | water | none | flash evaporation | solid | Form I |
| 23 | MeOH | none | flash evaporation | solid | Form I |
| 24 | EtOH | none | flash evaporation | solid | Form I |
| 25 | heptane | none | flash evaporation | solid | Form II |
| 26 | EtOH | none | flash evaporation | solid | Form I |
| 27 | THF/water (82:18% v/v) | none | flash evaporation | solid | Form I |
| 28 | THF | none | slurry (5° C.) | solid | Form I |
| 29 | acetone | none | slurry (5° C.) | solid | Form I |
| 30 | DMSO | none | slurry (20° C.) | solid | Amorphous |
| 31 | EtOAc | none | slurry (5° C.) | solid | Form I |
| 32 | IPA | none | slurry (5° C.) | solid | Form I |
| 33 | water | none | slurry (5° C.) | solid | Form III |
| 34 | MeOH | none | slurry (5° C.) | solid | Form IV |
| 35 | EtOH | none | slurry (5° C.) | solid | Form I |
| 36 | heptane | none | slurry (5° C.) | solid | Amorphous |
| 37 | THF/water (82:18% v/v) | none | slurry (5° C.) | solid | Form I |
| 38 | THF | none | slurry (60° C.) | solid | Form I |
| 39 | acetone | none | slurry (60° C.) | solid | Amorphous |
| 40 | DMSO | none | slurry (60° C.) | solid | Form I |
| 41 | EtOAc | none | slurry (60° C.) | solid | Form I |
| 42 | IPA | none | slurry (60° C.) | solid | Form I |
| 43 | water | none | slurry (60° C.) | solid | Form III |
| 44 | MeOH | none | slurry (60° C.) | solid | Form I |
| 45 | EtOH | none | slurry (60° C.) | solid | Form I |
| 46 | heptane | none | slurry (60° C.) | solid | Amorphous |
| 47 | EtOH/water (96:4% v/v) | none | slurry (60° C.) | solid | Form I |
| 48 | THF | none | vapour stress | solid | Amorphous |
| 49 | acetone | none | vapour stress | solid | Amorphous |
| 50 | DMSO | none | vapour stress | solid | Amorphous |
| 51 | EtOAc | none | vapour stress | solid | Form I |
| 52 | IPA | none | vapour stress | solid | Form I |
| 53 | water | none | vapour stress | solid | Form I |
| 54 | MeOH | none | vapour stress | solid | Form I |
| 55 | EtOH | none | vapour stress | solid | Form I |
| 56 | heptane | none | vapour stress | solid | Amorphous |
| 57 | THF/water (82:18% v/v) | none | vapour stress | solution | |
| 58 | THF/water (82:18% v/v) | THF | vapour diffusion | solid | Form I |
| 59 | THF/water (82:18% v/v) | IPA | vapour diffusion | solid | Form I |
| 60 | THF/water (82:18% v/v) | EtOAc | vapour diffusion | solid | Form I |
| 61 | acetone/water (50:50% v/v) | none | slow cool | solid | Form I |
| 62 | DMSO/water (80:20% v/v) | none | slow cool | solid | Form I |
| 63 | water | none | slow cool | solid | Form III |
| 64 | IPA/water (80:20% v/v) | none | slow cool | solid | Form I |
| 65 | MEOH/water (84:16% v/v) | none | slow cool | solid | Form I |
| 66 | THF/water (82:18% v/v) | none | slow cool | solid | Form I |
| 67 | THF/water (82:18% v/v) | none | crash precipitation | solid | Form I |
| 68 | DMSO | THF | crash precipitation | no solid | — |
| 69 | DMSO | EtOAc | crash precipitation | solid | Amorphous |
| 70 | THF/water (82:18% v/v) | none | temperature cycle | solid | Form I |
| 71 | DMSO/water (80:20% v/v) | none | temperature cycle | solid | Form I |
| 72 | MeOH/water (84:16% v/v) | none | temperature cycle | solid | Form I |

*amorphous material as starting material

A further crystalline form V was obtained during salt formation process development.

X-ray diffraction (XRD) analysis was performed on a Malvern Panalytical Empyrean S3 diffractometer. Instrument operating conditions for X-ray pattern acquisition were as follows:

| Program | |
| --- | --- |
| Type | Malvern Panalytical Empyrean S3 |
| Generator setting | 45 kV, 40 mA |
| Geometry mode | Transmission |
| Incident beam optics | |
| PreFix module | FDS |
| Soller slit | Soller 0.04 rad |
| Fixed Divergence slit | Slit fixed ½° |
| Fixed Anti-scatter slit | Slit fixed ½° |
| Diffracted beam optics | |
| Detector | PIXcel$^{1D}$ |
| Scan mode | Continuous |
| Soller slit | Soller 0.04 rad |
| Mask | 7.5 mm |
| Filter | Ni |
| Program | |
| Scan range | 2-40° (2θ) |
| Step size | 0.007° (2θ) |
| Step time | 24 s |
| Sample rotation | 1 rps |

The following tables 6-9 disclose the list of XRPD pics of Forms II-V.

TABLE 6

| Form II | |
| --- | --- |
| Angle 2-Thêta (°) | Relative Intensity % |
| 21.37 | 100.00 |
| 23.73 | 32.25 |

TABLE 7

| Form III | |
| --- | --- |
| Angle 2-Thêta (°) | Relative Intensity % |
| 14.01 | 100.00 |
| 16.94 | 54.02 |
| 20.31 | 47.22 |
| 22.52 | 40.32 |
| 28.32 | 32.54 |
| 34.16 | 25.35 |
| 35.25 | 9.73 |
| 38.28 | 10.71 |

TABLE 8

| Form IV | |
| --- | --- |
| Angle 2-Thêta (°) | Relative Intensity % |
| 2.03 | 100.0 |
| 10.32 | 15.63 |
| 11.02 | 24.77 |
| 12.48 | 17.98 |
| 13.95 | 20.17 |
| 14.23 | 12.46 |
| 16.67 | 16.80 |
| 17.47 | 9.63 |
| 18.03 | 11.77 |
| 21.65 | 10.46 |
| 22.14 | 16.77 |
| 22.60 | 18.28 |
| 23.73 | 9.35 |
| 24.00 | 33.40 |
| 24.42 | 13.15 |

TABLE 9

| Form V | |
| --- | --- |
| Angle 2-Thêta (°) | Relative Intensity % |
| 3.95 | 100.00 |
| 4.13 | 21.28 |
| 8.39 | 11.09 |
| 12.00 | 10.25 |
| 13.15 | 19.24 |
| 13.92 | 76.21 |
| 14.37 | 33.84 |
| 15.03 | 25.51 |
| 16.16 | 19.14 |
| 16.60 | 76.29 |
| 17.01 | 54.40 |
| 17.50 | 25.27 |
| 17.97 | 15.71 |
| 18.60 | 12.05 |
| 22.75 | 48.48 |
| 23.20 | 31.54 |
| 24.00 | 19.50 |
| 24.41 | 12.54 |
| 25.02 | 29.30 |
| 26.01 | 22.99 |
| 27.85 | 24.12 |
| 28.75 | 12.71 |
| 29.21 | 17.91 |
| 33.17 | 10.47 |

Example 2: Solubility Studies

Material and Method

The solubility kinetics of the salt forms as well as the native EYP001 free acid form were determined in FaSSIF and FeSSIF media, and in a pH 4.5 acetate buffer as detailed below:

| Test medium | Composition | Measured pH |
| --- | --- | --- |
| pH 4.5 acetate buffer (50 mM) | 0.299 g of sodium acetate trihydrate + 1.4 mL of 2M CH$_3$COOH in a 100 mL volumetric flask. Complete to 100 mL with de-ionized water. (note: the pH needed to be slightly adjusted to 4.5 with 1N HCl) | 4.5 |
| FaSSIF (29 mM) | 0.042 g of NaOH pellets + 0.395 g of NaH$_2$PO$_4$, H2O + 0.619 g of NaCl in a 100 mL volumetric flask. Complete to 100 mL with de-ionized water. (note: the pH needed to be slightly adjusted to 6.5 | 6.5 |

| Test medium | Composition | Measured pH |
|---|---|---|
| | with 1N NaOH). Then 0.112 g of Biorelevant powder in a 50 mL volumetric flask. Complete to 50 mL with blank FaSSIF. | |
| FeSSIF | 0.404 g of NaOH pellets + 0.865 g of acetic acid + 1.187 g of NaCl in a 100 mL volumetric flask. Complete to 100 mL with de-ionized water. (note: the pH needed to be slightly adjusted to 5.0 with 1N NaOH). Then 0.56 g of Biorelevant powder in a 50 mL volumetric flask. Complete to 50 mL with FeSSIF buffer. | 5.0 |

The samples were prepared by adding an excess of each tested bulk (salt or native EYP001) to a given volume of test medium. The suspension was stirred by orbital stirring over 1 hour (in both pH 4.5 acetate buffer and FeSSIF medium) or 24 hours (in FaSSIF medium) at 37° C., protected from light.

In pH 4.5 acetate buffer, the soluble concentration was assessed after 0.5 hour and 1 hour of stirring.

In FaSSIF medium, the soluble concentration was assessed after 24 hours of stirring. In FeSSIF medium, the soluble concentration was assessed after 0.5 hours and 1 hour of stirring.

At each time point, the "supernatant" was isolated and diluted in a solvent mixture allowing its injection into the chromatographic system. The concentration in solution in the test medium was determined by HPLC with external standardization.

Results

The results of the solubility kinetics in pH 4.5 acetate buffer, FaSSIF (Fasted State Stimulated Intestinal Fluid) and FeSSIF (Fed State Stimulated Intestinal Fluid) media are presented in the following Tables 10-12.

TABLE 10

| | Soluble fraction (expressed in mg/mL of EYP001) at 37° C. in pH 4.5 acetate buffer | |
|---|---|---|
| Sample | After 0.5 h | After 1 h |
| EYP001 free acid | 0.004 | 0.003 |
| EYP001 Benethamine salt (polymorph I) | 0.001 | 0.001 |
| EYP001 Benethamine salt (polymorph II) | 0.0002 | 0.0003 |
| EYP001 Zinc salt | 0.004 | 0.004 |
| EYP001 Benzathine salt | <0.001 | <0.001 |
| EYP001 Ethylene diamine salt | 0.003 | 0.003 |
| EYP001 L-Lysine salt (Form I) | 0.010 | 0.006 |

TABLE 11

| Sample | Soluble fraction (expressed in mg/mL of EYP001) at 37° C. in FaSSIF medium after 24 h |
|---|---|
| EYP001 free acid | 0.20 (pH = 6.4) |
| EYP001 Piperazine salt | ND |
| EYP001 Morpholine salt | 0.22 (pH = 6.5) |
| EYP001 Imidazole salt (Polymorph I) | 0.23 (pH = 6.5) |
| EYP001 Imidazole salt (Polymorph II) | 0.25 (pH = 6.5) |
| EYP001 Benethamine salt (Polymorph I) | 0.01 (pH = 6.6) |
| EYP001 Benethamine salt (Polymorph II) | 0.01 (pH = 6.5) |
| EYP001 Zinc salt | 0.22 (pH = 6.5) |
| EYP001 Cyclohexylamine salt (Polymorph II) | 0.19 (pH = 6.5) |
| EYP001 L-Lysine salt (Form I) | 0.31 (pH = 6.6) |

ND: Not determined

TABLE 12

| | Soluble fraction (expressed in mg/mL of EYP001) at 37° C. in FeSSIF medium | |
|---|---|---|
| Sample | After 0.5 h | After 1 h |
| EYP001 free acid | 0.38 (pH = 4.9) | 0.45 (pH = 6.4) |
| EYP001 Potassium salt | 0.35 (pH = 5.0) | 0.38 (pH = 5.0) |
| EYP001 L-Lysine salt (Form I) | 0.44 (pH = 5.0) | 0.46 (pH = 5.0) |

Conclusion:

As shown in Table 10, EYP001 L-lysine salt displayed a much higher solubility in the pH 4.5 acetate buffer compared to EYP001 free acid, EYP001 Benethamine salt, EYP001 Zinc salt, EYP001 Benzathine salt and EYP001 Ethylene diamine salt. In the FaSSIF medium, EYP001 L-lysine salt showed also a higher solubility compared to EYP001 free acid, EYP001 Piperazine salt, EYP001 Morpholine salt, EYP001 Imidazole salt, EYP001 Benethamine salt, EYP001 Zinc salt, and EYP001 Cyclohexylamine salt (Table 11). In the FeSSIF medium, EYP001 L-lysine salt also showed a higher solubility compared to EYP001 free acid and EYP001 Potassium salt (Table 12).

Example 3: Pharmacokinetic Study

Material and Method

In a first study (Experiment #1), EYP001, EYP001 Meglumine salt, and EYP001 L-lysine salt in aqueous formulations (0.5% CMC, 0.25% Tween 80, water) were orally administered at a dose of 50 mg $Eq_{EYP001}$/Kg in 3 male rats for each compound. Blood samples were taken at 0.25 h, 0.5 h, 1 h, 2 h, 4 h, 6 h, 8 h, 12 h, and 24 h after oral administration.

In a second study (Experiment #2), EYP001 and EYP001 L-lysine salt in aqueous formulations (0.5% CMC, 0.25% Tween 80, water) were orally administered at a dose of 50 mg $Eq_{EYP001}$/Kg in 8 male rats for each compound. Blood samples were taken at 0.25 h, 0.5 h, 1 h, 2 h, 4 h, 6 h, 8 h, 12 h, and 24 h after oral administration.

Results

The results of the PK study are presented in the following Tables 13A and 13B.

TABLE 13A

| | Experiment #1 | | | |
|---|---|---|---|---|
| Compound | Mean $AUC_{0-24}$ (hr*ng/mL) | % increase/ EYP001 | Mean Cmax (ng/ml) | % increase/ EYP001 |
| EYP001 free acid | 52306 SD: 6804.8 CV %: 13.0 | | 6990 SD: 242.6 CV %: 3.5 | |
| EYP001 Meglumine salt | 33076 SD: 7821.1 CV %: 23.6 | | 5372 SD: 2275.9 CV %: 42.4 | |
| EYP001 L-Lysine salt (Form I) | 60011 SD: 17217.2 CV %: 28.7 | +15% | 8827 SD: 880.2 CV %: 10.0 | +26% |

ND: Not determined
SD: Standard Deviation
CV %: % of relative standard deviation

TABLE 13B

| | Experiment #2 | | | |
|---|---|---|---|---|
| Compound | Mean $AUC_{0-24}$ (hr*ng/mL) | % increase/ EYP001 | Mean Cmax (ng/ml) | % increase/ EYP001 |
| EYP001 free acid | 29007 SD: 5416 CV %: 19 | | 5581 SD: 2202 CV %: 39 | |
| EYP001 L-Lysine salt (Form I) | 42500 SD: 8046 CV %: 19 | +47% | 7870 SD: 1610 CV %: 20 | +41% |

ND: Not determined
SD: Standard Deviation
CV %: % of relative standard deviation

CONCLUSION

As described in Table 13A, EYP001 L-lysine salt showed superior exposure ($AUC_{0-24}$) and higher Cmax compared to EYP001 free acid and EYP001 Meglumine salt in Experiment #1. Those results, showing the superiority of EYP001 L-lysine salt were confirmed in a second study (Experiment #2) using a higher number of animals (Table 13B).

The invention claimed is:

1. An L-lysine salt of 4-chloro-5-[4-(2,6-dichlorophenyl)sulfonylpiperazin-1-yl]-1-benzofuran-2-carboxylic acid in a crystalline form, wherein the X-ray diffraction pattern of the crystalline form comprises peaks at diffraction angles 2-Theta (2θ) of: 7.6°±0.2°, 10.1°±0.2°, 12.6°±0.2°, 15.1°±0.2°, 17.6°±0.2°, and 20.1°±0.2°, and wherein the X-ray diffraction pattern is obtained with a Cu Kα anode.

2. An L-lysine salt of 4-chloro-5-[4-(2,6-dichlorophenyl)sulfonylpiperazin-1-yl]-1-benzofuran-2-carboxylic acid in a crystalline form, wherein the X-ray diffraction pattern of the crystalline form comprises peaks at diffraction angles 2-Theta (2θ) of: 5.2°±0.2°, 7.6°±0.2°, 10.1°±0.2°, 11.6°±0.2°, 12.6°±0.2°, 13.7°±0.2°, 15.1°±0.2°, 16.3°±0.2°, 17.1°±0.2°, 17.6°±0.2°, 19.2°±0.2°, 20.1°±0.2°, 20.9°±0.2°, 22.1°±0.2°, 23.3°±0.2°, 24.0°±0.2°, 24.5°±0.2°, 25.9°±0.2°, 27.8°±0.2°, 28.7°±0.2°, 29.3°±0.2°, 30.3°±0.2°, 35.5°±0.2°, and 38.1°±0.2°, and wherein the X-ray diffraction pattern is obtained with a Cu Kα anode.

3. An L-lysine salt of 4-chloro-5-[4-(2,6-dichlorophenyl)sulfonylpiperazin-1-yl]-1-benzofuran-2-carboxylic acid in a crystalline form, wherein the X-ray diffraction pattern of the crystalline form comprises peaks of:

| Angle 2-Thêta (°) | Inter-reticular distance (Å) | Intensity c.p.s. | Intensity % |
|---|---|---|---|
| 5.2 | 17.1 | 2621 | 12.8 |
| 7.6 | 11.7 | 7592 | 37.2 |
| 8.6 | 10.2 | 472 | 2.3 |
| 9.1 | 9.7 | 563 | 2.8 |
| 10.1 | 8.8 | 13162 | 64.5 |
| 11.6 | 7.6 | 3002 | 14.7 |
| 12.6 | 7.0 | 15458 | 75.7 |
| 13.7 | 6.5 | 1636 | 8.0 |
| 14.2 | 6.3 | 1200 | 5.9 |
| 14.4 | 6.1 | 1447 | 7.1 |
| 15.1 | 5.9 | 20420 | 100.0 |
| 15.9 | 5.6 | 714 | 3.5 |
| 16.3 | 5.4 | 2179 | 10.7 |
| 16.6 | 5.3 | 454 | 2.2 |
| 17.1 | 5.2 | 2009 | 9.8 |
| 17.6 | 5.0 | 16409 | 80.4 |
| 18.4 | 4.8 | 801 | 3.9 |
| 18.8 | 4.7 | 1255 | 6.1 |
| 19.2 | 4.6 | 1586 | 7.8 |
| 20.1 | 4.4 | 9957 | 48.8 |
| 20.5 | 4.3 | 1145 | 5.6 |
| 20.9 | 4.2 | 3149 | 15.4 |
| 21.7 | 4.1 | 948 | 4.6 |
| 22.1 | 4.0 | 1717 | 8.4 |
| 23.3 | 3.8 | 3652 | 17.9 |
| 24.0 | 3.7 | 2548 | 12.5 |
| 24.5 | 3.6 | 1778 | 8.7 |
| 24.8 | 3.6 | 971 | 4.8 |
| 25.1 | 3.5 | 1029 | 5.0 |
| 25.9 | 3.4 | 2887 | 14.1 |
| 26.7 | 3.3 | 624 | 3.1 |
| 27.8 | 3.2 | 3360 | 16.5 |
| 28.4 | 3.1 | 641 | 3.1 |
| 28.7 | 3.1 | 1184 | 5.8 |
| 29.0 | 3.1 | 713 | 3.5 |
| 29.3 | 3.0 | 1928 | 9.4 |
| 30.3 | 2.9 | 4176 | 20.5 |
| 30.9 | 2.9 | 447 | 2.2 |
| 31.2 | 2.9 | 506 | 2.5 |
| 31.6 | 2.8 | 459 | 2.2 |
| 32.7 | 2.7 | 336 | 1.6 |
| 33.2 | 2.7 | 466 | 2.3 |
| 33.7 | 2.7 | 372 | 1.8 |
| 34.1 | 2.6 | 538 | 2.6 |
| 34.9 | 2.6 | 413 | 2.0 |
| 35.5 | 2.5 | 2284 | 11.2 |
| 36.3 | 2.5 | 688 | 3.4 |
| 36.6 | 2.5 | 460 | 2.3 |
| 36.9 | 2.4 | 362 | 1.8 |
| 37.4 | 2.4 | 346 | 1.7 |
| 38.1 | 2.4 | 1043 | 5.1 |
| 38.8 | 2.3 | 391 | 1.9 |
| 40.5 | 2.2 | 514 | 2.5 |
| 40.9 | 2.2 | 315 | 1.5 |
| 41.3 | 2.2 | 369 | 1.8 |
| 42.5 | 2.1 | 335 | 1.6 |
| 43.0 | 2.1 | 342 | 1.7 |
| 43.5 | 2.1 | 315 | 1.5 |
| 43.7 | 2.1 | 489 | 2.4 |
| 44.9 | 2.0 | 364 | 1.8 |
| 45.3 | 2.0 | 304 | 1.5 |
| 45.6 | 2.0 | 310 | 1.5 |
| 46.1 | 2.0 | 337 | 1.7 |
| 47.7 | 1.9 | 327 | 1.6 |
| 48.5 | 1.9 | 251 | 1.2 |
| 48.9 | 1.9 | 266 | 1.3 |
| 49.2 | 1.9 | 276 | 1.4 | and wherein the X-ray diffraction pattern is obtained with a Cu Kα anode.

4. A process for preparing the crystalline L-lysine salt according to claim 1, comprising steps of:
   a) contacting a solution of 4-chloro-5-[4-(2,6-dichlorophenyl)sulfonylpiperazin-1-yl]-1-benzofuran-2-carboxylic acid in THF with a solution of L-lysine in ethanol/water or in water; and
   b) isolating the crystalline form obtained in the step a).

5. The process according to claim 4, further comprising a step of temperature cycling, wherein 4-chloro-5-[4-(2,6-dichlorophenyl)sulfonylpiperazin-1-yl]-1-benzofuran-2-carboxylic acid:L-lysine stoichiometry in the step a) is 1:1.

6. A pharmaceutical or veterinary composition comprising the crystalline L-lysine salt according to claim 1, and a pharmaceutically acceptable excipient.

7. The pharmaceutical or veterinary composition according to claim 6, further comprising an additional therapeutic agent.

8. The pharmaceutical or veterinary composition according to claim 7, wherein the additional therapeutic agent is at least one selected from the group consisting of a TLR3 agonist, a TLR7 agonist, a TLR8 agonist, a TLR9 agonist, a RIG-I modulator, a STING agonist, an antiviral agent, an antibacterial agent, an interferon or a pegylated form thereof, a checkpoint inhibitor, an ERA, an ACE inhibitor, an ARB, a RASS antagonist, a beta-blocker, a diuretic agent, a MRA, a SGLT2 inhibitor, a GLP1 agonist, a SGLT1 inhibitor, FGF19, FGF21, a DPP-4 inhibitor, a PPAR agonist, a THR beta agonist, a FASN, and an inhibitor of HSD17b13.

9. A method of treating a disease selected from the group consisting of a chronic liver disease, a gastrointestinal disease, a renal disease, a cardiovascular disease, a metabolic disease, an infection, a cancer, and an autoimmune disease, the method comprising administering to a subject in need thereof the crystalline L-lysine salt according to claim 1, or a pharmaceutical composition comprising said crystalline L-lysine salt and a pharmaceutically acceptable excipient.

10. The method according to claim 9, wherein the disease is the infection.

11. The method according to claim 9, wherein the disease is an infection by hepatitis B virus (HBV), hepatitis C virus (HCV), hepatitis D virus (HDV), herpes simplex virus (HSV), papillomavirus (HPV), varicella-zoster virus, cytomegalovirus (CMV), rhinoviruses, hepatitis A virus, hepatitis E virus, Kaposis sarcoma herpesvirus, coronavirus, SARS-Cov1, MERS-Cov and SARS-Cov2, retrovirus HIV, or an influenza virus.

12. The method according to claim 10, wherein said compound or composition is administered in combination with at least one selected from the group consisting of a TLR3 agonist, a TLR7 agonist, a TLR8 agonist, a TLR9 agonist, a RIG-I modulator, a STING agonist, an antiviral agent, an antibacterial agent, an interferon or a pegylated form thereof, and a checkpoint inhibitor.

13. The method according to claim 9, wherein the disease is renal fibrosis, hypertension, type 2 diabetes, type 1 diabetes, obesity, Non-Alcoholic Steatohepatitis (NASH), non-alcoholic fatty liver disease (NAFLD), metabolic (dysfunction) associated fatty liver disease (MAFLD), ageing, infectious glomerulonephritis, focal segmental glomerulosclerosis, IgA nephropathy, minimal change glomerulopathy, membranous nephropathy, renal vasculitis, urinary tract obstruction, genetic alterations, autoimmune disease, systemic lupus erythematosus (SLE), drug- or toxin-induced nephropathy, AIDS-associated nephropathy, ischemic nephropathy, tubulointerstitial nephropathy, hepatorenal syndrome, hydronephrosis, renal dysplasia, medullary cystic kidney disease, medullary sponge kidney, multicystic dysplastic kidney, podocytopathy, kidney papillary necrosis, nephritis, glomerulonephritis, hereditary nephritis, interstitial nephritis, pyelitis, nephrocalcinosis, nephrosclerosis, Alport syndrome cystinosis, classical homocystinuria (HCU), Fabry's disease, renal sarcoidosis, diabetic nephropathy, focal segmental glomerulosclerosis (FSGS), hypertensive nephrosclerosis, chronic glomerulonephritis, chronic transplant glomerulopathy, chronic interstitial nephritis, Sjogren's syndrome, Alagille syndrome, alpha 1-antitrypsin deficiency, or polycystic kidney disease.

14. The method according to claim 13, wherein said compound or composition is administered in combination with at least one selected from the group consisting of an ERA, an ACE inhibitor, an ARB, a RASS antagonist, a beta-blocker, a diuretic agent, a MRA, a SGLT2 inhibitor, and a GLP1 agonist.

15. The method according to claim 9, wherein the disease is primary biliary cirrhosis, primary biliary cholangitis (PBC), cerebrotendinous xanthomatosis (CTX), primary sclerosing cholangitis (PSC), drug induced cholestasis, intrahepatic cholestasis of pregnancy, parenteral nutrition associated cholestasis (PNAC), bacterial overgrowth or sepsis associated cholestasis, autoimmune hepatitis, chronic viral hepatitis, alcoholic liver disease, nonalcoholic fatty liver disease (NAFLD), nonalcoholic steatohepatitis (NASH), alcoholic hepatitis, liver transplant associated graft versus host disease, living donor transplant liver regeneration, congenital hepatic fibrosis, choledocholithiasis, granulomatous liver disease, intra- or extrahepatic malignancy, Sjogren's syndrome, Alagille syndrome, Sarcoidosis, Wilson's disease, Gaucher's disease, hemochromatosis, biliary atresia, ductopenic liver transplant rejection, cystic fibrosis liver disease or alpha 1-antitrypsin deficiency.

16. The method according to claim 15, wherein said compound or composition is administered in combination with at least one selected from the group consisting of a SGLT2 inhibitor, a GLP1 agonist, a SGLT1 inhibitor, FGF19, FGF21, a DPP-4 inhibitor, a PPAR agonist, a THR beta agonist, a FASN, and an inhibitor of HSD17b13.

17. A method of treating Chronic Kidney Disease (CKD), comprising administering to a subject in need thereof the crystalline L-lysine salt according to claim 1, or a pharmaceutical composition comprising said crystalline L-lysine salt and a pharmaceutically acceptable excipient.

18. The method according to claim 17, wherein said compound or composition is administered in combination with at least one selected from the group consisting of an ERA, an ACE inhibitor, an ARB, a RASS antagonist, a beta-blocker, a diuretic agent, a MRA, a SGLT2 inhibitor, and a GLP1 agonist.

19. A process for preparing the crystalline L-lysine salt according to claim 2, comprising steps of:
   a) contacting a solution of 4-chloro-5-[4-(2,6-dichlorophenyl)sulfonylpiperazin-1-yl]-1-benzofuran-2-carboxylic acid in THF with a solution of L-lysine in ethanol/water or in water; and
   b) isolating the crystalline form obtained in the step a).

20. The process according to claim 19, further comprising a step of temperature cycling, wherein 4-chloro-5-[4-(2,6-dichlorophenyl)sulfonylpiperazin-1-yl]-1-benzofuran-2-carboxylic acid:L-lysine stoichiometry in the step a) is 1:1.

21. A pharmaceutical or veterinary composition comprising the crystalline L-lysine salt according to claim 2, and a pharmaceutically acceptable excipient.

22. The pharmaceutical or veterinary composition according to claim 21, further comprising an additional therapeutic agent.

23. The pharmaceutical or veterinary composition according to claim 22, wherein the additional therapeutic agent is at least one therapeutic agent selected from the group consisting of a TLR3 agonist, a TLR7 agonist, a TLR8 agonist, a TLR9 agonist, a RIG-I modulator, a STING agonist, an antiviral agent, an antibacterial agent, an interferon or a pegylated form thereof, a checkpoint inhibitor, an ERA, an ACE inhibitor, an ARB, a RASS antagonist, a beta-blocker, a diuretic agent, a MRA, a SGLT2 inhibitor, a GLP1 agonist, a SGLT1 inhibitor, FGF19, FGF21, a DPP-4 inhibitor, a PPAR agonist, a THR beta agonist, a FASN, and an inhibitor of HSD17b13.

24. A method of treating a disease selected from the group consisting of a chronic liver disease, a gastrointestinal disease, a renal disease, a cardiovascular disease, a metabolic disease, an infection, a cancer, and an autoimmune disease, the method comprising administering to a subject in need thereof the crystalline L-lysine salt according to claim 2, or a pharmaceutical composition comprising said crystalline L-lysine salt and a pharmaceutically acceptable excipient.

25. The method according to claim 24, wherein the disease is an infection.

26. The method according to claim 25, wherein the disease is an infection by hepatitis B virus (HBV), hepatitis C virus (HCV), hepatitis D virus (HDV), herpes simplex virus (HSV), papillomavirus (HPV), varicella-zoster virus, cytomegalovirus (CMV), rhinoviruses, hepatitis A virus, hepatitis E virus, Kaposis sarcoma herpesvirus, coronavirus, SARS-Cov1, MERS-Cov and SARS-Cov2, retrovirus HIV, or an influenza virus.

27. The method according to claim 25, wherein said compound or composition is administered in combination with at least one selected from the group consisting of a TLR3 agonist, a TLR7 agonist, a TLR8 agonist, a TLR9 agonist, a RIG-I modulator, a STING agonist, an antiviral agent, an antibacterial agent, an interferon or a pegylated form thereof, and a checkpoint inhibitor.

28. The method according to claim 24, wherein the disease is a renal fibrosis, hypertension, type 2 diabetes, type 1 diabetes, obesity, Non-Alcoholic Steatohepatitis (NASH), non-alcoholic fatty liver disease (NAFLD), metabolic (dysfunction) associated fatty liver disease (MAFLD), ageing, infectious glomerulonephritis, focal segmental glomerulosclerosis, IgA nephropathy, minimal change glomerulopathy, membranous nephropathy, renal vasculitis, urinary tract obstruction, genetic alterations, autoimmune disease, systemic lupus erythematosus (SLE), drug- or toxin-induced nephropathy, AIDS-associated nephropathy, ischemic nephropathy, tubulointerstitial nephropathy, hepatorenal syndrome, hydronephrosis, renal dysplasia, medullary cystic kidney disease, medullary sponge kidney, multicystic dysplastic kidney, podocytopathy, kidney papillary necrosis, nephritis, glomerulonephritis, hereditary nephritis, interstitial nephritis, pyelitis, nephrocalcinosis, nephrosclerosis, Alport syndrome cystinosis, classical homocystinuria (HCU), Fabry's disease, renal sarcoidosis, diabetic nephropathy, focal segmental glomerulosclerosis (FSGS), hypertensive nephrosclerosis, chronic glomerulonephritis, chronic transplant glomerulopathy, chronic interstitial nephritis, Sjogren's syndrome, Alagille syndrome, alpha 1-antitrypsin deficiency, or polycystic kidney disease.

29. The method according to claim 28, wherein said compound or composition is administered in combination with at least one selected from the group consisting of an ERA, an ACE inhibitor, an ARB, a RASS antagonist, a beta-blocker, a diuretic agent, a MRA, a SGLT2 inhibitor, and a GLP1 agonist.

30. The method according to claim 24, wherein the disease is primary biliary cirrhosis, primary biliary cholangitis (PBC), cerebrotendinous xanthomatosis (CTX), primary sclerosing cholangitis (PSC), drug induced cholestasis, intrahepatic cholestasis of pregnancy, parenteral nutrition associated cholestasis (PNAC), bacterial overgrowth or sepsis associated cholestasis, autoimmune hepatitis, chronic viral hepatitis, alcoholic liver disease, nonalcoholic fatty liver disease (NAFLD), nonalcoholic steatohepatitis (NASH), alcoholic hepatitis, liver transplant associated graft versus host disease, living donor transplant liver regeneration, congenital hepatic fibrosis, choledocholithiasis, granulomatous liver disease, intra- or extrahepatic malignancy, Sjogren's syndrome, Alagille syndrome, Sarcoidosis, Wilson's disease, Gaucher's disease, hemochromatosis, biliary atresia, ductopenic liver transplant rejection, cystic fibrosis liver disease or alpha 1-antitrypsin deficiency.

31. The method according to claim 30, wherein said compound or composition is administered in combination with at least one selected from the group consisting of a SGLT2 inhibitor, a GLP1 agonist, a SGLT1 inhibitor, FGF19, FGF21, a DPP-4 inhibitor, a PPAR agonist, a THR beta agonist, a FASN, and an inhibitor of HSD17b13.

32. A method of treating Chronic Kidney Disease (CKD), comprising administering to a subject in need thereof the crystalline L-lysine salt according to claim 2, or a pharmaceutical composition comprising said crystalline L-lysine salt and a pharmaceutically acceptable excipient.

33. The method according to claim 32, wherein said compound or composition is administered in combination with at least one selected from the group consisting of an ERA, an ACE inhibitor, an ARB, a RASS antagonist, a beta-blocker, a diuretic agent, a MRA, a SGLT2 inhibitor, and a GLP1 agonist.

34. A process for preparing the crystalline L-lysine salt according to claim 3, comprising steps of:
   a) contacting a solution of 4-chloro-5-[4-(2,6-dichlorophenyl)sulfonylpiperazin-1-yl]-1-benzofuran-2-carboxylic acid in THF to a solution of L-lysine in ethanol/water or in water; and
   b) isolating the crystalline form obtained in the step a).

35. The process according to claim 34, further comprising a step of temperature cycling, wherein 4-chloro-5-[4-(2,6-dichlorophenyl)sulfonylpiperazin-1-yl]-1-benzofuran-2-carboxylic acid:L-lysine stoichiometry in the step a) is 1:1.

36. A pharmaceutical or veterinary composition comprising the crystalline L-lysine salt according to claim 3, and a pharmaceutically acceptable excipient.

37. The pharmaceutical or veterinary composition according to claim 36, further comprising an additional therapeutic agent.

38. The pharmaceutical or veterinary composition according to claim 37, wherein the additional therapeutic agent is at least one selected from the group consisting of a TLR3 agonist, a TLR7 agonist, a TLR8 agonist, a TLR9 agonist, a RIG-I modulator, a STING agonist, an antiviral agent, an antibacterial agent, an interferon or a pegylated form thereof, a checkpoint inhibitor, an ERA, an ACE inhibitor, an ARB, a RASS antagonist, a beta-blocker, a diuretic agent, a MRA, a SGLT2 inhibitor, a GLP1 agonist, a SGLT1 inhibitor, FGF19, FGF21, a DPP-4 inhibitor, a PPAR agonist, a THR beta agonist, a FASN, and an inhibitor of HSD17b13.

39. A method of treating a disease selected from the group consisting of a chronic liver disease, a gastrointestinal disease, a renal disease, a cardiovascular disease, a metabolic disease, an infection, a cancer, and an autoimmune disease, the method comprising administering to a subject in need thereof the crystalline L-lysine salt according to claim 3, or a pharmaceutical composition comprising said crystalline L-lysine salt and a pharmaceutically acceptable excipient.

40. The method according to claim 39, wherein the disease is an infection.

41. The method according to claim 39, wherein the disease is an infection by hepatitis B virus (HBV), hepatitis C virus (HCV), hepatitis D virus (HDV), herpes simplex virus (HSV), papillomavirus (HPV), varicella-zoster virus, cytomegalovirus (CMV), rhinoviruses, hepatitis A virus, hepatitis E virus, Kaposis sarcoma herpesvirus, coronavirus, SARS-Cov1, MERS-Cov and SARS-Cov2, retrovirus HIV, or an influenza virus.

42. The method according to claim 40, wherein said compound or composition is administered in combination with at least one selected from the group consisting of a TLR3 agonist, a TLR7 agonist, a TLR8 agonist, a TLR9 agonist, a RIG-I modulator, a STING agonist, an antiviral agent, an antibacterial agent, an interferon or a pegylated from thereof, and a checkpoint inhibitor.

43. The method according to claim 39, wherein the disease is a renal fibrosis, hypertension, type 2 diabetes, type 1 diabetes, obesity, Non-Alcoholic Steatohepatitis (NASH), non-alcoholic fatty liver disease (NAFLD), metabolic (dysfunction) associated fatty liver disease (MAFLD), ageing, infectious glomerulonephritis, focal segmental glomerulosclerosis, IgA nephropathy, minimal change glomerulopathy, membranous nephropathy, renal vasculitis, urinary tract obstruction, genetic alterations, autoimmune disease, systemic lupus erythematosus (SLE), drug- or toxin-induced nephropathy, AIDS-associated nephropathy, ischemic nephropathy, tubulointerstitial nephropathy, hepatorenal syndrome, hydronephrosis, renal dysplasia, medullary cystic kidney disease, medullary sponge kidney, multicystic dysplastic kidney, podocytopathy, kidney papillary necrosis, nephritis, glomerulonephritis, hereditary nephritis, interstitial nephritis, pyelitis, nephrocalcinosis, nephrosclerosis, Alport syndrome cystinosis, classical homocystinuria (HCU), Fabry's disease, renal sarcoidosis, diabetic nephropathy, focal segmental glomerulosclerosis (FSGS), hypertensive nephrosclerosis, chronic glomerulonephritis, chronic transplant glomerulopathy, chronic interstitial nephritis, Sjogren's syndrome, Alagille syndrome, alpha 1-antitrypsin deficiency, or polycystic kidney disease.

44. The method according to claim 43, wherein said compound or composition is administered in combination with at least one selected from the group consisting of an ERA, an ACE inhibitor, an ARB, a RASS antagonist, a beta-blocker, a diuretic agent, a MRA, a SGLT2 inhibitor, and a GLP1 agonist.

45. The method according to claim 39, wherein the disease is primary biliary cirrhosis, primary biliary cholangitis (PBC), cerebrotendinous xanthomatosis (CTX), primary sclerosing cholangitis (PSC), drug induced cholestasis, intrahepatic cholestasis of pregnancy, parenteral nutrition associated cholestasis (PNAC), bacterial overgrowth or sepsis associated cholestasis, autoimmune hepatitis, chronic viral hepatitis, alcoholic liver disease, nonalcoholic fatty liver disease (NAFLD), nonalcoholic steatohepatitis (NASH), alcoholic hepatitis, liver transplant associated graft versus host disease, living donor transplant liver regeneration, congenital hepatic fibrosis, choledocholithiasis, granulomatous liver disease, intra- or extrahepatic malignancy, Sjogren's syndrome, Alagille syndrome, Sarcoidosis, Wilson's disease, Gaucher's disease, hemochromatosis, biliary atresia, ductopenic liver transplant rejection, cystic fibrosis liver disease or alpha 1-antitrypsin deficiency.

46. The method according to claim 45, wherein said compound or composition is administered in combination with at least one selected from the group consisting of a SGLT2 inhibitor, a GLP1 agonist, a SGLT1 inhibitor, FGF19, FGF21, a DPP-4 inhibitor, a PPAR agonist, a THR beta agonist, a FASN, and an inhibitor of HSD17b13.

47. A method of treating Chronic Kidney Disease (CKD), comprising administering to a subject in need thereof the crystalline L-lysine salt according to claim 3, or a pharmaceutical composition comprising said crystalline L-lysine salt and a pharmaceutically acceptable excipient.

48. The method according to claim 47, wherein said compound or composition is administered in combination with at least one selected from the group consisting of an ERA, an ACE inhibitor, an ARB, a RASS antagonist, a beta-blocker, a diuretic agent, a MRA, a SGLT2 inhibitor, and a GLP1 agonist.

* * * * *

UNITED STATES PATENT AND TRADEMARK OFFICE
CERTIFICATE OF CORRECTION

PATENT NO. : 12,030,861 B1  
APPLICATION NO. : 18/351587  
DATED : July 9, 2024  
INVENTOR(S) : Raphaël Darteil et al.

Page 1 of 1

It is certified that error appears in the above-identified patent and that said Letters Patent is hereby corrected as shown below:

In the Specification

<u>Column 26,</u>  
Lines 34-35:  
" 57   THF/water   none   vapour stress   solution  
      (82:18% v/v) "

Should read:  
  57   THF/water   none   vapour stress   solution  —  
      (82:18% v/v)                                                    —.

Signed and Sealed this  
Twenty-second Day of July, 2025

Coke Morgan Stewart  
*Acting Director of the United States Patent and Trademark Office*